United States Patent [19]

Brode et al.

[11] Patent Number: 4,767,463

[45] Date of Patent: Aug. 30, 1988

[54] GLYCOSAMINOGLYCAN AND CATIONIC POLYMER COMBINATIONS

[75] Inventors: George L. Brode, Bridgewater, N.J.; Philip A. Band, Brooklyn, N.Y.; Errol D. Goddard, Somerville, N.J.; Arminda G. Barbone, Union, N.J.; Adolf Leshchiner, Fairview, N.J.; Joseph P. Pavlichko, Helmetta, N.J.; Emmett M. Partain, III, Bound Brook, N.J.; Pak S. Leung, Highland Mills, N.Y.

[73] Assignee: Union Carbide Corporation, Danbury, Conn.

[21] Appl. No.: 38,836

[22] Filed: Apr. 15, 1987

[51] Int. Cl.[4] .......................... C08L 1/00; A61K 7/09
[52] U.S. Cl. ...................................... 106/162; 424/70; 424/71; 106/203; 106/205; 106/208; 524/27
[58] Field of Search .................. 424/70, 71; 106/162, 106/203, 205, 208; 524/27

[56] References Cited

U.S. PATENT DOCUMENTS

| | | | |
|---|---|---|---|
| 3,472,840 | 10/1969 | Stone et al. | 536/43 |
| 4,240,450 | 12/1980 | Grollier et al. | 132/7 |
| 4,299,817 | 11/1981 | Hannan, III et al. | 424/70 |
| 4,501,834 | 2/1985 | Su | 524/28 |
| 4,657,820 | 4/1987 | Halpern et al. | 106/162 |
| 4,668,508 | 5/1987 | Grollier et al. | 424/71 |

OTHER PUBLICATIONS

Chem. Abst. 69:22331k, Cleland, 1968.
Balazs, E. A. and Band, P., "Hyaluronic Acid: Its Structure and Use", *Cosmetics and Toiletries*, Jun. 1984, vol. 99, pp. 65-81.
Band, P., "Effective Use of Hyaluronic Acid", *Drug and Cosmetic Industry*, Oct. 1985, vol. 137, pp. 54-56.
Petrak, K., "Polyelectrolye Complexes in Biomedical Applications", *J. of Bioactive and Compatible Polymers*, vol. 1, Apr. 1986, pp. 202-219.
Nakajima, A. and Shinoda, K., "Complex Formation between Oppositely Charged Polysaccharides", *J. of Colloid and Interface Science*, vol. 55, No. 1, Apr. 1976, pp. 126-132.

*Primary Examiner*—Theodore Morris
*Attorney, Agent, or Firm*—Henry H. Gibson

[57] ABSTRACT

Combinations of glycosaminoglycan and certain cationic polymers provide modified glycosaminoglycan properties and can provide substantivity to keratinous material, compatibility, stability, humectancy, rheology and other properties useful in personal care or medical applications.

23 Claims, No Drawings

GLYCOSAMINOGLYCAN AND CATIONIC POLYMER COMBINATIONS

BACKGROUND OF THE INVENTION

1. Field of the Invention

This invention relates to polymeric combinations and more particularly to combinations of glycosaminoglycan and cationic polymer and to processes for managing keratinous material and modifying glycosaminoglycan properties using such combinations.

2. Description of Background Information

Glycosaminoglycans provide significant utility in biological systems. Glycosaminoqlycans can provide high viscosity and elasticity when in aqueous solution by absorbing large volumes of water. In biological systems these properties enable glycosaminoglycans to stabilize and support fibrous components and cellular structures and contribute to water maintenance and salt balance in tissues. Various glycosaminoglycans have been utilized in medical and personal care applications. For example, one such glycosaminoglycan, hyaluronan, has a high capacity to hold water and provide a gel-like substance which exhibits unique properties characteristic of a true liquid by being capable of dilution and exhibiting viscous flow as well as elastic and pseudoplastic properties. As used herein, the terms "glycosaminoglycan" and "hyaluronan" include both the free acid and corresponding salt forms, consistent with accepted nomenclature as described by E. A. Balazs et al., *Biochemical Journal Letters,* Volume 235, p. 903 (1986). Detailed descriptions of the structure, properties and uses of hyaluronan are presented in the literature articles: Balazs, E.A. and Band, P., "Hyaluronic Acid: Its Structure and Use", *Cosmetics & Toiletries,* June 1984, Volume 99, Pages 65-81; and Band, P., "Effective Use of Hyaluronic Acid", *Drug and Cosmetic Industry,* October 1985, Volume 137, Pages 54-56.

The use of qlycosaminoglycans, such as hyaluronan, and the ability to take full advantage of the unique properties of such materials in certain medical and personal care applications is, however, limited by a general lack of substantivity of such material to keratinous substrates, such as hair, skin or like materials. Glycosaminoglycans, are anionic polymers, which disassociate in aqueous solution, providing a negative charge inhibiting its deposition and retention on similarly negatively charged, keratinous materials.

Various cationic polymers, such as quaternary nitrogen containing cellulose ethers, including those described in U.S. Pat. No. 3,472,840 (Stone, et al.), are substantive to keratinous materials. Such polymers are readily deposited and retained on keratinous materials such that the properties of such polymers have increased effect on the keratin in providing, for example, improved conditioning, manageability or other desirable properties.

Combinations of anionic and cationic polymers in general are known and described in personal care applications. U.S. Pat. No. 4,240,450 (Grollier, et al.) and various references cited therein, describe compositions containing anionic polymer, cationic polymer and surfactant in a solvent medium, for use in treating keratin materials. Grollier, et al. disclose that various anionic polymers may be anchored to keratin material when used in combination with cationic polymers. Various properties and applications of anionic and cationic polymer combinations are summarized in a review by Petrak, K., entitled "Polyelectrolyte Complexes in Biomedical Applications", in the *Journal of Bioactive and Compatible Polymers,* Vol. 1, April, 1986, pages 202-219. Hair care compositions containing the ionic reaction product of cationic and anionic polymers are described in U.S. Pat. No. 4,299,817, (Hannan III, et al.). Water soluble and water insoluble gels provided by interpolymer reactions of selective anionic and cationic polymers, useful in cosmetic compositions are described in U.S. Pat. No. 4,501,834 (Su). Polyelectrolyte complexes of hyaluronan and glycol chitosan, a cationic polymer, are described by A. Nakajima et al. in an article entitled "Complex Formation Between Oppositely Charged Polysaccharides" in the *Journal of Colloid and Interface Science,* Vol. 55, No. 1, April, 1976, pages 126-132.

Combinations of anionic and cationic polymers, however, are unpredictable in their ability to provide substantivity of the anionic polymer to keratinous material, as well as in their ability to provide a wide variety of properties either required or desirable for various medical or personal care applications. Compositions containing both anionic and cationic polymers, due in part to their contrasting electrical charge and resulting characteristics, are generally limited in their ability to provide compatible, stable solutions exhibiting useful rheological properties and/or substantivity, particularly when combined with typical additives used in personal care or medical products.

It would be desirable if compositions and processes could be provided which contain glycosaminoglycan and cationic polymer which are substantive to keratinous materials to maximize the benefits provided by both polymers. Such compositions and processes should have sufficient compatibility and stability to be useful in various solvent systems, and preferably provide rheological properties suitable for a wide range of end uses.

SUMMARY OF THE INVENTION

This invention pertains to combinations comprising cationic polymer and glycosaminoglycan as well as to particular embodiments of such combinations. Processes for modifying glycosaminoglycan properties and for managing keratinous material by applying an effective managing amount of such combinations to keratinous substrate are also provided.

DETAILED DESCRIPTION OF THE INVENTION

This invention pertains to combinations of, and processes using, glycosaminoglycan and cationic polymers which provide unique modification of the properties exhibited by the glycosaminoglycan. In particular, the properties provided by the glycosaminoglycan are increased or enhanced by combination with the cationic polymer. In addition, the glycosaminoglycan can be made substantive to keratinous material through the presence of the cationic polymer. Compositions and processes are also described which provide such combinations with compatibility, stability and exhibit rheological properties for utility in a wide variety of applications.

Cationic polymer and glycosaminoglycan combinations are provided which form uniform viscoelastic matrixes. These surface matrixes act as reenforcement when applied to keratinous substrate by generating highly flexible and strong structural films. This results in well hydrated substrate protected from environmental attack by the uniform surface covering, which can be retained even after water immersion. When applied to the skin, the combination has excellent rub in and afterfeel properties. The substantivity of the combination extends the time the glycosaminoglycan remains in contact with the keratinous substrate for delivering the benefits of the glycosaminoglycan to the substrate. Increased humectancy, i.e. moisturization, is provided using a hydrated matrix of cationic polymer and glycosaminoglycan taking advantage of glycosaminoglycan properties for holding water, such as has been demonstrated in intercellular matrix of dermal connective tissue.

Glycosaminoglycans are well known, naturally occurring, polysaccharides containing disaccharide repeating units of hexosamine and hexose or hexuronic acid, and may contain sulfate groups.

The size, type or form of glycosaminoglycan provided is not narrowly critical to this invention. The molecular weight of the glycosaminoglycan is not critical and may range from about 5,000 to about 20,000,000, preferably from about 100,000 to about 12,000,000, and most preferably from about 1,000,000 to about 10,000,000. Glycosaminoglycan may be provided in free acid or salt form. The glycosaminoglycate may be associated with any suitable cation, including, but not limited to: alkali metals, such as sodium and potassium; alkaline earth metals; nitrogen containing cations, such as ammonium, substituted ammonium and quaternized derivatives thereof; and other suitable cations. Preferred salts of glycosaminoglycans and derivatives thereof include alkali metal or alkaline earth metal glycosaminoglycates. The glycosaminoglycan may be provided: in pure form; as a mixture of glycosaminoglycan with proteins and naturally occurring substances derived by the production of glycosaminoglycan from natural material; or as a chemically modified, glycosaminoglycan derivative. Mixtures of such glycosaminoglycans may also be provided.

Representative glycosaminoglycans include, but are not limited to: hyaluronan or derivatives thereof such as hylan; heparin; heparan; chondroitin; keratan; dermatan; and sulfates of such materials. A particularly preferred glycosaminoglycan is hyaluronan, and derivatives thereof, which contain repeating disaccharide structure of D-glucuronic acid and 2 -acetamido-2-desoxy-D-glucose joined by alternating $\beta 1 \rightarrow 3$ glucuronidic and $\beta 1 \rightarrow 4$ glucosaminidic bonds. Representative hyaluronan and derivatives thereof which may be provided include, but are not limited to: BIOMATRIX ® hyaluronan provided by Biomatrix, Inc., such as described in U.S. Pat. No. 4,303,676 (Balazs) which is incorporated herein by reference, HYLADERM ® hylan provided by Biomatrix, Inc., such as described in U.K. Published Patent Application No. 2,172,295A (Balazs, et al.) which is incorporated herein by reference; and substantially pure hyaluronan such as described in U.S. Pat. No. 4,141,973 (Balazs) which is incorporated herein by reference.

In the broadest sense, any cationic polymer may be used which, when combined with glycosaminoglycan, provides a modification in the properties of the glycosaminoglycan, such as improved rheology, increased substantivity and preferably other desired properties. Such cationic polymers may be selected from within the class of cationic polymers which provide substantivity to keratinous material. Such cationic polymers may be either synthetic or naturally occurring materials. The synthetic polymers may be produced by addition or condensation polymerizations or may derived by chemical modification of naturally occurring polymers. The particular polymeric structure is not critical so long as the cationic polymer provides the requisite modification of glycosaminoglycan properties, and preferably additional desirable properties, as hereinafter discussed.

Representative cationic polymers which may be provided include, but are not limited to: polysaccharide, condensation polymer, polyalkylenimine, and homo- or copolymer of ethylenically unsaturated compounds; which polymer contains cationic substitution, such as by containing cationized nitrogen, phosphorus or sulfur groups. Representative polysaccharides include, but are not limited to: the starch and cellulose families; pectin; chitin; chitosan; guar; and the like. Representative polyalkylenimines include, but are not limited to; poly N-acyl alkylenimines, and hydrolyzed derivatives thereof. Representative homo- or copolymers of ethylenically unsaturated compounds include, but are not limited to: poly(meth)acrylamides, polyvinyl pyrrolidones, poly(meth)acrylates, diallyl dialkyl ammonium halides, as well as grafts or copolymers of such materials.

Preferred cationic polymers include, but are not limited to, water soluble polymers which may be selected from the following: quaternary nitrogen-containing cellulose ethers such as UCARE ® Polymers JR-125, JR-400, JR-30M, LR-400, LR-30M and SR-10 provided by Union Carbide Corp., and as described in U.S. Pat. No. 3,472,840 (Stone, et al.) which is incorporated herein by reference; hydrophobe modified, quaternary nitrogen-containing polysaccharides, such as QUATRISOFT TM Polymers provided by Union Carbide Corp., and as described European Published Patent Application No. 189,935 which is incorporated herein by reference; graft copolymers of cellulose ethers and dialkyl diallyl ammonium halide, such as CELQUAT ® Polymers provided by National Starch; quaternarized nitrogen-substituted galactomannan, such as JAGUAR ® Polymers provided by Celanese; homo- and copolymers of dialkyl diallyl ammonium halide, such as MERQUAT ® Polymers provided by Calgon; copolymers of vinyl pyrrolidone and quaternized dialkylaminoalkyl methacrylate such as GAFQUAT ® Polymers provided by GAF Corp.; copolymers of acrylamide and quaternized, dialkyl amino dialkyl methacrylate, such as RETEN ® Polymers provided by Hercules, Inc.; and other cationic polymers including polymers identified as polyquaternium compounds by the Cosmetics, Toiletries and Fragrance Association (CTFA).

Particularly preferred cationic polymers include certain water soluble, quaternary nitrogen containing polysaccharides represented by the overall structural formula:

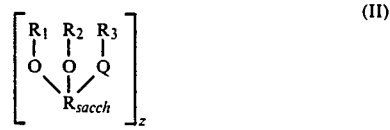

(II)

In Formula II, $R_{sacch}$ is the residue of a polysaccharide repeat unit. The polysaccharide repeat unit may contain more than three "R" substituents for those polysaccharides which contain more than three reactive hydroxyl groups per repeat unit. $R_{sacch}$ is preferably the residue of an anhydroglucose repeat unit, particularly from cellulose.

The parameter Q in Formula II varies depending upon the particular polysaccharide being utilized. For example, Q is —O— when the particular polysaccharide comprises anhydroglucose repeat units such as in starch, cellulose or the like. Similarly, Q is:

wherein $R_4$ is

in chitin and wherein $R_4$ is a mixture of hydrogen and

groups in chitosan. Q is preferably —O—, i.e. an oxygen atom.

The number of polysaccharide repeat units, defined by z in Formula II, is usually from about 50 to about 20,000, preferably from about 100 to about 6,000; and most preferably from about 250 to about 4,000. The corresponding molecular weights of the cationic polysaccharide will usually range from several thousand up to several million.

The $R_1$, $R_2$ and $R_3$ substituents in Formula II are either hydrogen, when representing unreacted hydroxyl groups of the polysaccharide, or substituents provided by etherification, quaternization and/or other derivitization. Each $R_1$, $R_2$ and $R_3$ is individually represented by the substituent structural formula:

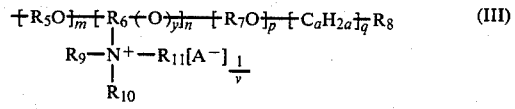

In Formula III, A is an anion, including mixtures of anions. Exemplary anions include inorganic anions such as chloride, bromide, iodide, sulfate, methylsulfate, sulfonate, nitrate, phosphate, and the like; and organic anions such as acetate, and the like. Monovalent anions are preferred, particularly halides, and especially chloride. The anions are typically provided as the residue of the quaternary ammonium salts used as quaternizing agents, or by other known techniques.

The alkylene substituent defined by a in Formula III, contains from 1 to about 3 carbon atoms such that a is an integer having a value of from 1 to about 3.

The extent of etherification due to oxyalkylene substituents, as defined by m and p in Formula III, generally ranges from 0 to about 6 oxyalkylene groups each, i.e. m is an integer of from 0 to about 6 and p is an integer of from 0 to about 6. The additional extent of etherification, as defined by q in Formula II, depends upon the absence or presence of the alkylene group, i.e. $C_aH_{2a}$, such that q is 0 or 1, preferably 0.

The total extent of etherification, as measured in terms of molar substitution, i.e., MS, is usually greater than 0, generally from about 1.2 to about 4.5, and preferably from about 1.8 to about 3.6.

The number of quaternary nitrogen atoms per substituent, defined by n in Formula III, is greater than or equal to 0, i.e. n is an integer greater than or equal to 0. The extent of quaternization throughout the polysaccharide, characterized as the degree of cationic substitution, i.e. CS, provides an average value per repeat unit which is greater than 0, and in some embodiments is generally less than 1 and preferably from about 0.01 to about 0.6.

Each $R_5$ and $R_7$ in Formula III, defining the oxyalkylene substituent, is individually an ethylene (providing oxyethylene), a propylene (providing oxypropylene) or a hydroxypropylene (providing hydroxy substituted oxypropylene) unit. $R_5$ and $R_7$ are preferably ethylene or hydroxypropylene, and most preferably ethylene.

The segment connecting the quaternary nitrogen to the polysaccharide molecule, defined as $R_6$ in Formula III, is a di or a trivalent, cyclic, branched or straight chain, saturated or unsaturated hydrocarbon having from 2 to about 6 carbon atoms, provided that there are at least 2 carbon atoms between the nitrogen atom and any oxygen atom, such as in the ether substituent or polysaccharide residue. $R_6$ can be ethylene, a $C_3$ hydrocarbon group, —CH$_2$CH=CHCH$_2$—, or when combined with $R_9$, $R_{10}$ or $R_{11}$ can be cycloalkyl suc as

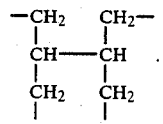

Most preferably $R_6$ is

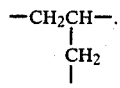

$R_8$ in Formula III is hydrogen, hydroxyl, a hydrophobic group $R_h$, alkyl, carboxyl, alkali metal or amine carboxylate, or other terminal group provided that when q is 0 then $R_8$ is hydrogen or alkyl. $R_8$ is preferably hydrogen or alkyl. When $R_8$ is hydrogen and m, n, p and q are all 0 the substituent structural formula provides an unsubstituted polysaccharide hydroxyl group.

The nitrogen substituents, defined by $R_9$, $R_{10}$ and $R_{11}$ in Formula II, are each individually a hydrophobic group $R_h$, alkyl, aryl, aralkyl, alkaryl, cycloalkyl, alkoxyalkyl, alkoxyaryl or together with $R_6$ form a nitrogen-containing heterocyclic ring. If an alkoxyalkyl or alkoxyaryl substituent is provided, at least two carbon atoms separate the substituent oxygen atom from the nitrogen atom. Nitrogen substituents include: lower alkyls having from 1 to about 3 carbon atoms, such as methyl, or ethyl; aryls such as phenyl; aralkyls such as benzyl; or, together with $R_6$, dialkyl substituted cycloalkyl such as N,N-dimethyl pyrrolidyl; and the like. Preferred nitrogen substituents of each repeat unit are methyl, a hydrophobic group, or together with $R_6$ provide a pyrrolidyl, or are a mixture of such groups.

When present, the hydrophobic group, defined by $R_h$, contains a long chain alkyl group having at least 8 carbon atoms, preferably from about 10 to about 24 carbon atoms, and most preferably from about 10 to about 18 carbon atoms. The hydrophobic group is attached directly to the quaternary nitrogen when present as $R_9$, $R_{10}$ or $R_{11}$; to the ether substituent $R_8$; and/or directly to the polysaccharide residue as $R_8$ when m, n, p and q are all zero. The hydrophobic group may be provided at any or all of these locations, in the same or different repeat units within the polysaccharide molecule. The hydrophobic group may also contain a connecting segment between the alkyl group and the nitrogen or oxygen atom to which the group is connected, depending upon the alkylating agent used to connect the alkyl group to the polysaccharide. The hydrophobic group is preferably a long chain alkyl group bonded directly to a nitrogen or oxygen atom, and most preferably to the quaternary nitrogen.

The valence of anion A, defined as v in Formula III, is an integer, preferably 1.

The absence or presence of the ether oxygen in the quaternary nitrogen substituent is defined by y in Formula III, i.e., y is 0 or 1, respectively, provided that in the absence of further ether substitution, i.e. when n is greater than 0 and y is 0, then p and q are 0 and $R_8$ is hydrogen. Preferably y is 1.

Illustrative of some of the numerous possible substituents for an individual polysaccharide repeat unit include the following:

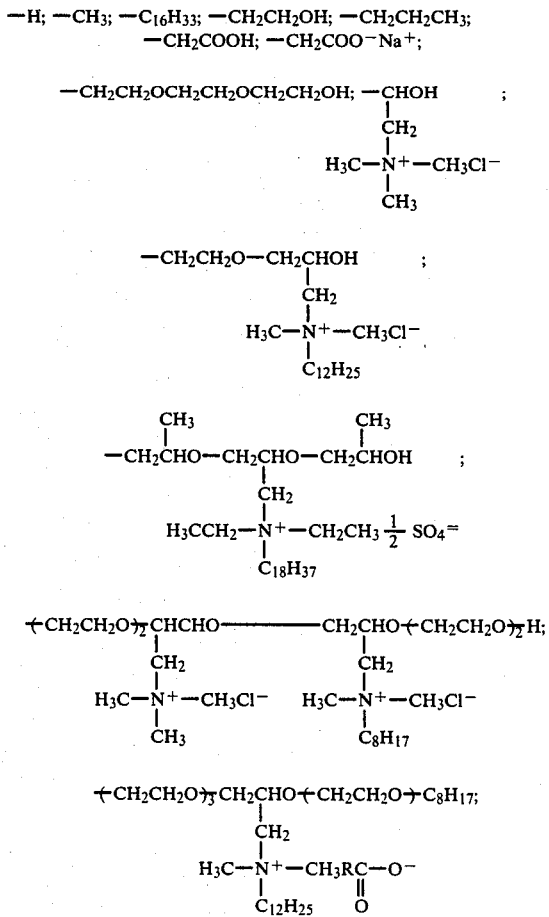

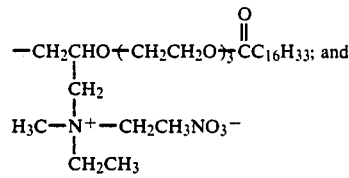

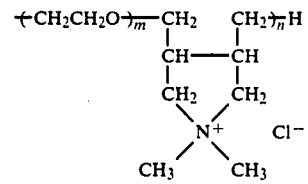

wherein R is lower alkyl, and m and n are as defined previously.

In a preferred embodiment, the cationic polymer is a cellulose ether represented by the overall structural formula:

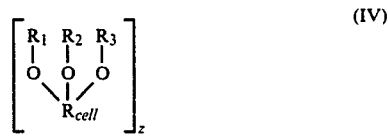

wherein:
$R_{cell}$ is the residue of an anhydroglucose repeat unit; and z, $R_1$, $R_2$ and $R_3$ are as defined previously except for the further provisos that:
(1) the extent of hydrophobic group substitution, HS, defined by the average moles of said hydrophobic groups per mole of polysaccharide repeat unit, is greater than 0; or
(2) any one of $R_9$, $R_{10}$ or $R_{11}$ taken together with $R_6$ forms a heterocyclic ring and the average value of n per polysaccharide repeat unit, is greater than 0.

The specific amount of glycosaminoglycan provided is not narrowly critical. Generally, an effective managing amount, which is defined as that amount of glycosaminoglycan sufficient to provide effective or improved keratin treatment utility to the combination, is provided. Typically, the amount of glycosaminoglycan is at least about 0.0001 wt. %, preferably from about 0.0005 wt. % to about 2 wt. %, and most preferably from about 0.001 wt. % to about 1 wt. % of the total composition.

The specific amount of cationic polymer provided is not critical, so long as an effective amount sufficient to modify glycosaminoglycan performance, as hereinafter discussed, is provided. Typically, the amount of cationic polymer is at least about 0.0005 wt. % preferably from about 0.0025 wt. % to about 20 wt. %, and most preferably from about 0.005 wt. % to about 10 wt. % of the total composition.

In the broadest sense, the relative proportion of cationic polymer to glycosaminoglycan is not narrowly critical except that an effective amount of cationic polymer is provided which is sufficient to modify glycosaminoglycan properties. The relative weight ratio of cationic polymer to glycosaminoglycan will generally range from about 0.01:1 to about 200:1, preferably from about 2:1 to about 100:1, and most preferably from about 10:1 to about 50:1.

Variations in the relative weight ratio of cationic polymer to glycosaminoglycan can provide properties including improved glycosaminoglycan rheology and substantivity, as well as compatibility, enhanced feel and extended stability. An enhanced degree of glycosaminoglycan substantivity can be provided when applied to keratinous substrate, such as hair or skin. Enhanced substantivity to skin may be provided at relative weight ratios of cationic polymer to glycosaminoglycan of greater than about 5:1, and preferably from about 35:1 to about 75:1. Enhanced glycosaminoglycan substantivity to hair can be provided using relative weight ratios of cationic polymer to glycosaminoglycan of from about 5:1 to about 25:1. The relative weight ratios providing enhanced substantivity can vary depending upon the type and amount of cationic polymer and glycosaminoglycan, as well as the presence and amount of additional ingredients, such as surfactants or other personal care compounds.

The glycosaminoglycan and cationic polymer combination provides a unique and surprising modification in the properties of the glycosaminoglycan. In the broadest sense, this modification in glycosaminoglycan properties is characterized by an increase or enhancement in the properties exhibited by the glycosaminoglycan which may include, but is not limited to, its rheology or substantivity to keratinous material.

Modification of glycosaminoglycan performance can be determined through analysis of the properties provided by the glycosaminoglycan through comparison with and without the presence of the cationic polymer. In particular, glycosaminoglycan properties, such as providing compositions with superior feel characteristics, are provided having substantially reduced concentrations of glycosaminoglycan when in combination with cationic polymer of this invention.

The glycosaminoglycan and cationic polymer combination can also provide substantivity of the glycosaminoglycan to keratinous material. The substantivity of this invention does not simply pertain to the properties of the cationic polymer but extends to the glycosaminoglycan in that the composition provides substantivity of glycosaminoglycan to keratinous material.

Substantivity of the glycosaminoglycan and cationic polymer combination is characterized by an increase in the deposition or retention, or both, of the glycosaminoglycan on keratinous material due to the presence of the cationic polymer, as compared to deposition or retention of an equivalent amount and kind of glycosaminoglycan on keratinous material in the absence of the cationic polymer.

Substantivity can be measured through analysis of radiolabelled glycosaminoglycan. In particular, tritiated glycosaminoglycan containing 6-$^3$H-D-glucosamine units may be provided, using well established techniques such as in vitro tissue culture methodology. When such radiolabelled glycosaminoglycan is applied to keratinous substrates the degree of substantivity can be determined by measuring the amount of glycosaminoglycan deposited or retained on the substrate through detecting the amount of radioactivity on the treated keratin. Substantivity can also be determined using electrokinetic streaming potential analysis, such as described in an article by Somasundaran et al., *J. Colloid Interface Science,* Vol. 45, 591 (1973). In particular, from measurement of the electrokinetic potential of hair samples treated with a combination of cationic polymer and glycosaminoglycan using a large excess of cationic polymer, it can be inferred that substantivity of glycosaminoglycan in a bound complex with the cationic polymer is achieved. Substantivity is determined through detection of adsorption and retention of the cationic polymer through electrokinetic potential analysis of such a combination. In addition, a change in electrokinetic streaming potential caused by application of glycosaminoglycan after an initial application of cationic polymers also shows substantivity of the glycosaminoglycan.

The glycosaminoglycan and cationic polymer combination can also possess desirable compatibility, stability and/or rheology.

Compatibility, as defined in this invention, is characterized by glycosaminoglycan/cationic polymer combinations which provide a homogeneous, single phase composition, such as an aqueous solution in which no precipitation occurs over at least a 24 hour period after combining the glycosaminoglycan and cationic polymer.

Compatibility can be determined through optical or viscosity analysis. In particular, the absorbance of compositions of glycosaminoglycan and cationic polymer can be measured, such as through visible absorbance measurements generally taken at 540 nanometers, initially and over 24 hours. Compositions which do not possess compatibility form a precipitate or provide decreasing absorbance of the remaining soluble composition within 24 hours. Compatibility can also be determined by measuring the viscosity of compositions of glycosaminoglycan and cationic polymer or dilutions thereof. Incompatible compositions provide solutions where the remaining soluble composition exhibits a reduction in viscosity within 24 hours.

Stability, as defined in this invention, is characterized by glycosaminoglycan and cationic polymer combinations which provide compositions possessing minimal destabilization over time or after freezing and thawing, such as through avoiding the formation of precipitates or coacervates, loss of homogeneity or a change in rheological properties.

Storage stability can be determined by analyzing glycosaminoglycan and cationic polymer combinations under controlled conditions, such as for several, such as four, months at various temperatures, such as 4° C., through visual observation of homogeneity, precipitate or coacervate and by optical, viscosity or other rheological measurement, using established procedures. Long term stability is demonstrated for samples exhibiting little or no change in properties. Freeze thaw stability can be determined using similar analyses of such combinations subjected to repeated freezing and thawing cycles.

Rheology, as defined in this invention, is characterized by viscosity, elasticity or other rheological properties of glycosaminoglycan and cationic polymer compositions, such as through analysis of compositions of glycosaminoglycan and cationic polymer with respect to viscosity as a function of shear rate and modulus of elasticity as a function of frequency of oscillation, using established procedures. Such compositions exhibit synergistic increases in shear viscosity and modulus of elasticity when compared with the sum of such values provided by the same type and amount of cationic polymer and glycosaminoglycan individually. The degree of enhanced rheology will generally vary depending upon the type and amount of cationic polymer and glycosaminoglycan, the relative weight ratio thereof, as well as the presence and amount of other compounds.

The presence and degree of compatibility, stability, and rheology provided by the glycosaminoglycan and cationic polymer combination will generally vary depending upon the particular type and form of glycosaminoglycan and cationic polymer, and relative proportions of the two components, and will be influenced by the presence and amount of other material effecting the interaction between the glycosaminoglycan and cationic polymer.

The glycosaminoglycan and cationic polymer combination of this invention provides utility in kericare applications. The term kericare as used in this invention describes the treatment or care of keratinous material, such as hair, skin, nails or other like material, and encompasses both medical and personal care applications.

Illustrative medical uses of this invention include, but are not limited to, the following: viscosurgery; coatings to improve the biocompatability of various materials; wound dressings; various pharmaceutical preparations; drug delivery; and other medical applications.

Illustrative personal care uses of this invention include, but are not limited to, the following: skin creams including cleansing, night, massage, moisturizing, vanishing, foundation, hand, hand-and-body, all-purpose creams and other known skin creams; astringents and skin tonics, including compositions for irritated, inflamed, allergic, hypersensitive or sensitized skin; protective creams and hand cleansers; bath preparations including foam baths, bath salts, bath oils, after bath products, and other known bath preparations; baby skin and hair products; adolescent skin products, such as for oily skin or acne, and other known adolescent skin products; antiperspirants and deodorants; depilatories; shaving preparations including wet shaving creams, sticks, foams, dry shaving lotions, powder, after shave lotions, foams, aerosols, gels, creams, balms and powders, and other known shaving preparations; foot preparations including foot powders, sprays, creams, corn, callus and chilblain and athlete's foot preparations and other known foot preparations; insect repellants; sunscreen, suntan and anti-sunburn preparations; skin lighteners or bleaches; face packs or masks including wax-, rubber-, vinyl-, hydrocolloid- or earth-based systems, anti-wrinkle preparations and other known face packs or masks; perfumes; face powders and make-up; colored make up preparations including lipstick, lip salves, rouge, eye make-up such as mascara, eye shadow, eye liner and other known make-up preparations; shampoos including clear liquids, liquid creams or lotions, solid creams or gels, oils, powders, aerosols, dry, conditioning, baby, anti-dandruff and medicated, acid-balanced shampoos and other known shampoos; hair setting preparations including lotions, sprays, dressings, brilliantines, fixatives, aerosols, emulsions, gels, and other known hair preparations; hair tonics and conditioners including rinses; hair colorants including temporary, semi-permanent, permanent or other hair dyes or colorants, hair dye removers, bleaches, lighteners and other known hair colorants; permanent wave and hair strengtheners; hair straighteners including caustic preparations, chemical hair reducing preparations and other known hair straighteners; dental products including dentifrices such as tooth paste, tooth gels, tooth powders, solid dentifrice, denture cleansers, adhesives, and other known dental products; mouth washes; and other known personal care uses.

The glycosaminoglycan and cationic polymer combination of this invention may also be useful in applications other than kericare, such as various timed-release applications.

The glycosaminoglycan and cationic polymer, or both, may be provided in suitable carrier, including mixtures of carriers, which acts as a fluid vehicle for the glycosaminoglycan and/or cationic polymer, as well as for suitable, optional ingredients. The type of carrier is not critical and may be selected from any carrier suitable to the particular application. Illustrative carriers include, but are not limited to: water, such as deionized or distilled water; emulsions, such as oil-in-water or water-in-oil emulsions; alcohols, such as ethanol, isopropanol or the like; glycols, such as propylene glycol, glycerine or the like; and mixtures thereof. Preferred carrier systems include water-in-oil or oil-in-water emulsions, water, ethanol and aqueous ethanol mixtures.

The glycosaminoglycan and cationic polymer combination may optionally contain suitable ingredients or additives typical of kericare compositions, which may be prepared following well established practices in the art. Illustrative ingredients which may be suitable include, but may not be limited to, the following, including mixtures thereof.

Illustrative surfactants may include: anionics such as fatty acid soaps, alkyl sulfates, alkyl ether sulfates, alkyl aryl sulfonates, sarcosinates, alkyl glucose esters or their alkoxylates and preferably sodium lauryl sulfate, ammonium lauryl sulfate, triethanol amine lauryl sulfate, sodium laureth sulfate, triethanol amine stearate, methyl glucose stearates or their ethoxylates and glycerol monostearate; nonionics such as fatty acid alkanol amides, alkyl aryl polyglycol ether, polyglycol ethers and preferably cocamide DEA, nonoxynol-7 and octoxynol-9; cationics such as alkyl trimethyl ammonium salts, quaternized amides of ethylene diamine, alkyl pyridinium salts and preferably cetrimonium chloride, stearalkonium chloride and cetyl pyridinium chloride; and amphoterics such as alkyl $\beta$-aminopropionates, betaines, alkyl imidazolines and preferably cocamidopropyl betaine and caproamphocarboxypropionate. Illustrative cleansers may include natural oils and alcohols and preferably mineral oil, lanolin oil, ethanol and isopropanol. Illustrative colorants may include pigments, dyes, and preferably FD&C Blue No. 1, FD&C No. 1 Aluminum Lake or similar sets of green, red or yellow. Illustrative preservatives may include alcohols, aldehydes, p-hydroxybenzoates and preferably methylparaben, propylparaben, glutaraldehyde and ethyl alcohol. Illustrative moisturizers may include alkyl glucose alkoxylates or their esters, fatty alcohols, fatty esters, glycols and preferably methyl glucose ethoxylates or propoxylates and their stearate esters, isopropyl myristate, lanolin or cetyl alcohols, propylene glycol, glycerol and sorbitol. Illustrative pH adjustors may include inorganic and organic acids and bases and preferably aqueous ammonia, citric acid, phosphoric acid, acetic acid, triethanolamine and sodium hydroxide. Illustrative emulsifiers may include anionic and nonionic surfactants and preferably stearic acid, glycerol monostearate, cocoyl diethanolamide, and the preferred anionic and nonionic surfactants listed previously. Illustrative propellants may include hydrocarbons, fluorocarbons, ethers, carbon dioxide, nitrogen and dimethyl ether. Illustrative reducing agents may include ammonium thioglycolate and sodium thioglycolate. Illustrative thickeners may include sodium chloride, hydroxyethyl cellulose, hydroxypropyl methyl cellulose, sodium carboxymethyl cellulose and polymers containing hydrophobe bunches including hydrophobe modified polyurethanes or other such polymers described in U.S. Pat. No. 4,426,485.

Other typical ingredients may include, but may not be limited to, the following: fragrances; foaming agents; sunscreen and suntan agents; depilatory agents; flavors; astringent agents; antiseptics; deodorants; antiperspirants; insect repellants; bleaches and lighteners; antidandruff agents; adhesives; polishes; strengtheners for hair, nails, or the like; fillers; barrier materials; and other known kericare additives. Mixtures of such ingredients may also be provided.

The amount of optional ingredients contained in the combinations of this invention is not critical but will vary depending upon the particular ingredient, composition and desired use level and may be any effective amount for achieving the desired property provided by such ingredients, following well established procedures known to those in the art.

Compositions of glycosaminoglycan and cationic polymer combination of this invention may be produced by providing the glycosaminoglycan or cationic polymer, or both, along with optional ingredients, such as any one or more suitable ingredients as previously described, to one or more suitable carriers. The glycosaminoglycan and cationic polymer may be provided comprising or consisting essentially of both components either separately as two compositions or combined in a single composition. When used separately, the glycosaminoglycan may be applied either simultaneously or sequentially to the application of cationic polymer. Typically, the cationic polymer is provided prior to, or along with, the application glycosaminoglycan.

The following examples are presented as illustrative embodiments of this invention and are not intended to limit the scope thereof. Unless stated otherwise all percentages are given in weight percent.

EXAMPLES

The various designations used in the examples are defined as follows:

| Designation | Description |
|---|---|
| Anionic Polymer I | Sodium salt of carboxymethyl cellulose having a degree of carboxymethyl substitution of between 0.4–1.0 and a 2 wt. % Brookfield viscosity of between 200–800 cP. |
| Cationic Polymer I | N—dodecyl, N,N—dimethyl quaternary ammonium chloride substituted hydroxyethyl cellulose, having a degree of cationic substitution of approximately 0.1, a 1 wt. % aqueous solution viscosity of 150–300 cP (Brookfield Model LVT, Spindle #2, 60 rpm) and an ash content (NaCl) of about 3 wt. %. |
| Cationic Polymer II | A graft copolymer of hydroxyethyl cellulose and dimethyl diallyl ammonium chloride, having a CTFA designation of Polyquaternium-4, available from National Starch under the trademark CELQUAT ® Polymer, grade H-100. |
| Cationic Polymer III | A graft copolymer of hydroxyethyl cellulose and dimethyl diallyl ammonium chloride, having a CTFA designation of Polyquaternium-4, available from National Starch under the trademark CELQUAT ® Polymer, grade L-200. |
| Cationic | A copolymer of vinyl pyrrolidone and |
| Polymer IV | diethylsulfate quaternized dimethylaminoethyl methacrylate, having a CTFA designation of Polyquaternium-11, available from GAF Corp. under the trademark GAFQUAT ® Polymer, grade 755N. |
| Cationic Polymer V | A homopolymer of dimethyl diallyl ammonium chloride, having a CTFA designation of Polyquaternium-6, available from Calgon Corp. under the trademark MERQUAT ® Polymer, grade 100. |
| Cationic Polymer VI | A copolymer of acrylamide and dimethyl diallyl ammonium chloride, having a CTFA designation of Polyquaternium-7, available from Calgon Corp. under the trademark MERQUAT ® Polymer, grade 550. |
| Cationic Polymer VII | N,N,N—trimethyl ammonium chloride substituted hydroxethyl cellulose, having a 2 wt. % Brookfield viscosity of between 300–500 cP and a wt. % N of about 0.8–1.1 |
| Cationic Polymer VIII | N,N,N—trimethyl ammonium chloride substituted hydroxethyl cellulose, havin a 2 wt. % Brookfield viscosity of between 300–500 cP and a wt. % N of about 1.8. |
| Glycosaminoglycan I | Sodium salt of hylan, produced by in situ reaction of aldehyde with naturally occurring hyaluronan in rooster comb following the procedures described in U.K. Published Patent Application No. 2,172,295A, having a viscosity number in excess of 4,000 cc per gram (measured at 80 μg per ml. of glycosaminoglycan in a 0.15 N sodium chloride solvent at 25° C., available from Biomatrix, Inc. under the trademark HYLADERM ®. |
| Glycosaminoglycan II | Sodium salt of hyaluronan having a viscosity number in excess of 4,000 cc per gram (measured at 80 μg per ml. of glycosaminoglycan in a 0.15 N sodium chloride solvent at 25° C.), available as an 0.5–0.6 wt. % aqueous solution in admixture with proteins and other naturally occuring substances, as described in U.S. Pat. No. 4,303,676 (Balazs), available from Biomatrix, Inc. under the trademark BIOMATRIX ® HA. |
| Glycosaminoglycan III | Heparin available from Sigma Chemical Co. |
| Glycosaminoglycan IV | Chondroitin sulfate available from Sigma Chemical Co. |
| Nonionic Polymer I | Hydroxyethyl cellulose having a hydroxyethyl molar substitution of between 2.0–2.5 and having a 2 wt. % Brookfield viscosity of between 300–400 cP, available from Union Carbide Corp. under the trademark CELLOSIZE ® QP-300. |
| Preservative I | A 27–29 wt. % solution of mixed esters of methyl, ethyl, propyl and butyl paraben in phenoxyethanol solvent, available from Nipa Laboratories under the trademark PHENONIP ®. |
| Preservative II | N—(hydroxymethyl)-N—(1,3-dihydroxymethyl-2,5-dioxo-4-imidazolidinyl)-N'—(hydroxymethyl) urea, having a CTFA designation of Diazolidinyl urea, available from Sutton Laboratories under the trademark GERMALL ® II. |
| Solvent I | Phenoxyethanol. |
| Surfactant I | Sodium laureth-3 sulfate available from Henkel Corp. as 28.5 wt. % aqueous solution under the trademark STANDAPOL ES 3. |
| Surfactant II | A 9–10 mole (average) ethoxylate of p-(1,1,3,3-tetramethylbutyl) phenol available from Aldrich Chemical Co. under the trademark TRITON ® X-100. |
| Surfactant | A cocoamphocarboxypropionate, available |

-continued

| Designation | Description |
| --- | --- |
| III | from Miranol Corp. as a 39 wt. % aqueous solution under the trademark MIRANOL ® C2M-SF Concentrate. |
| Surfactant IV | A 20 mole (average) ethoxylate of 9-octadecen-ol, having a CTFA designation of Oleth-20, available from Amerchol Corp. under the trademark AMEROXOL ® OE-20. |
| Surfactant V | A cocobetaine, available from Henkel Corp. as a 43.5 wt. % aqueous solution under the trademark VELVETEX ® AB-45. |
| Surfactant VI | A 20 mole (average) ethoxylate of methyl glucose sesquistearate, having a CTFA designation of Methyl gluceth-20 sesquistearate, available from Amerchol Corp. under the trademark GLUCAMATE ® SSE-20. |
| Surfactant VII | A 16 mole (average) ethoxylate of lanolin alcohol, having a CTFA designation of Laneth-16, available from Amerchol Corp. under the trademark SOLULAN ® 16. |
| Surfactant VIII | A 9 mole (average) ethoxylate of a mixture of $C_{11-15}$ alkanols, available from Union Carbide Corp. under the trademark TERGITOL ® 15-S-9. |
| Scintillation Complement | A toluene solution containing fluors and balancing acidic solubilizer, available from Isolab, Inc. under the tradename Unisol ® Complement. |
| Tissue Solubilizer | A quaternary ammonium hydroxide available from Isolab, Inc. under the tradename Unisol ® |

Unless otherwise indicated, the following test procedures are used to measure product and performance characteristics listed in the examples.

Compatibility: After cleared of air bubbles by centrifugation at 2000 rpm for 10 minutes, samples of aqueous solutions of glycosaminoglycan and cationic polymer combinations are measured for visible absorbance immediately after preparation of the solution, at a wavelength of 540 nanometers using distilled water as a control. The samples, in cuvettes, are then covered and refrigerated. At least one day later, the cuvettes are allowed to return to room temperature and the absorbance measurements are repeated. Compatibility is generally demonstrated by the absence of a significant drop in absorbance in the repeat measurement due to precipitation or coacervation.

Feel: A small amount of designated test composition is applied to the volar forearm, preferably at a hairless site, or to the back of the hand, keeping the test site consistent between comparisons, and rubbed into the skin. The characteristics of the composition which are evaluated include feel, rub-in, afterfeel of the treated skin, appearance of skin, along with any other noted characteristics.

Hair substantivity: Two procedures are used to determine hair substantivity.

1. Prior to using radiolabelled glycosaminoglycan, samples of blonde hair are prepared by washing in Surfactant II, followed by rinsing well first with tap water and then 3 times with distilled water. The hair samples are allowed to air dry and are cut into approximately 1 cm pieces. Samples of 100 mg of hair are placed in 7 ml glass scintillation vials and 1.0 ml of designated test solution of radiolabelled glycosaminoglycan is added to the sample vial followed by incubation for 1 hour with shaking. After the test solution is removed, the sample hair is rinsed 3 times with 5 ml distilled water per rinse. One ml of Tissue Solubilizer is added and the sample allowed to stand overnight at room temperature. The solubilized hair sample is transferred to a 20 ml glass scintillation vial with 0.5 ml methanol then 10 ml of Scintillation Complement is added. The radioactivity of the solubilized hair sample is measured using a ISO-CAP ® 300 liquid scintillation counter. The amount of glycosaminoglycan bound to the hair is presented as the percent of the disintegrations per minute, i.e. DPM, applied to the hair which is measured on washed and solubilized hair solution. Sequential testing is evaluated using the same procedure except that two designated text solutions, one of cationic polymer and the other of glycosaminoglycan, are used in a two step process. In the first step, the first designated test solution is incubated with shaking for 15 minutes, followed by rinsing the hair sample 3 times with 5 ml distilled water per rinse. The second step consists of adding 1 ml of the second designated test solution and then proceeding with 1 hour incubation and so on as described in the original procedure.

2. Using electrokinetic streaming potential analysis, a 6.6 g. sample of virgin hair is divided into 3 bundles. Each hair bundle is prepared for treatment by thoroughly wetting with tap water, applying 3 drops of Surfactant VIII which is manually worked into the hair for 30 seconds followed by rinsing first with tap water and then double distilled water. Samples of 1"-1.5" sections are cut, covered with double distilled water in crystallizing dishes and swirled around to insure the absence of air bubbles. The hair samples are placed in the bottom compartment of a U-shaped section of cell with air bubbles tapped out using a wire probe, and contained in the cell using porous platinum disc electrodes. The samples are rinsed 3 times with 100 ml of double distilled water per rinse using an aspirator to drain off liquid. The cells are filled with a weak electrolyte solution of $10^{-4}N$ $KNO_3$, which is passed through the hair for 5-minutes cycles and the streaming potential is measured to determine the zeta potential of the clear hair. The electrolyte solution is removed through aspiration and the cell filled with 300 ml of designated treating solution containing polymer(s). After 25 minutes of exposure to the treating solution, to allow adsorption of the polymers onto the hair to take place, the streaming potential is measured while passing the solution through the cell for 5 1-minute cycles to determine the zeta potential of hair covered with adsorbed polymers while still in contact with the polymer solution (Step 1). The treating solution is removed through aspiration and the hair rinsed 3 times with 100 ml of double distilled water per rinse and removed using aspiration after each cycle (Step 2). The cell is filled with 300 ml of $10^{-4}N$ $KNO_3$ solution (Step 3). The solution is passed back and forth through the hair for 1 hour with streaming potential measurements taken over this time period to determine the retention of adsorbed polymer on rinsing. Sequential polymer application is analyzed using the same procedure (Steps 1 and 2 above) except that a single polymer pre-treating solution is used. After rinsing (Step 2) the cell is filled with the second designated polymer treating solution after which the streaming potential is measured for one hour (Step 3). The electrokinetic (zeta) streaming potential is determined following established procedures, such as described in a paper by P. Somasundaran et al. in the *Journal of Colloid Interface Science*, Volume 45, page 591 (1973).

Modulus of elasticity: Measurements of designated test solutions are made over a frequency range of from 0.01 Hz to 5.0 Hz, using an oscillation strain amplitude of 5, performed at 25° C. using a Bohlin VOR rheometer equipped with a C-14 cup and spindle.

Shear viscosity: Measurements are made over a shear range of from 0.05 sec$^{-1}$ to 100 sec$^{-1}$, performed at 25° C. using a Bohlin VOR rheometer equipped with a C-14 cup and spindle.

Skin substantivity: Two procedures are used to determine skin substantivity.

1. Dried samples of stratum corneum taken from the skin of neonatal rats, having an average weight of 25 mg, are placed in 60 mm petri dishes, using 4 petri dishes per group totaling 100 mg stratum corneum. Two ml of designated test solution containing radiolabelled glycosaminoglycan are added to each petri dish which is incubated for 1 hour with gentle shaking. The test solution is then removed and the stratum corneum washed 3 times with 5 ml distilled water. All 4 strata corneum from each group are placed into a 20 ml glass scintillation vial along with 1 ml of Tissue Solubilizer added and allowed to stand overnight at room temperature. One-half ml of methanol then 10 ml of Scintillation Complement are added to the vials. The radiolabelled glycosaminoglycan bound to the solubilized tissue samples is measured using an ISOCAP ® 300 liquid scintillation counter. The weight, in micrograms ($\mu$g), of bound glycosaminoglycan is calculated from the measured radioactivity of the treated strata corneum and the measured specific activity of the radiolabelled glycosaminoglycan in DPM per $\mu$g. Sequential polymer application is analyzed using the same procedure except for the following modification: instead of a single 2 ml addition of test solution, 2 ml of first test solution is added to each petri dish followed by incubation for 30 minutes with gentle shaking. The strata corneum are then washed 3 times with distilled water and 2 ml of second test solution is added followed by 1 hour incubation and so on as in the original procedure.

2. Using electron spectroscopy, samples of strata corneum, treated substantially as described previously and air dried on TEFLON ® surface, are cut into approximately ½ × ½ inch squares and clamped to a sample platter using an aluminum mask. A 1×2 mm area is analyzed using standard electron spectroscopyic procedures such as described by M. K. Bahl, in the *Journal of Society of Cosmetic Chemists*, Volume 36, pages 287–296 (1985) and by E. D. Goddard and W. C. Harris, in the *Proceedings of the Fourteenth Congress of the International Federation of Societies of Cosmetic Chemists* (I.F.S.C.C.), Barcelona, Spain, Volume 2, 1039 (September 1986). Spectral measurements are made using a Surface Science Instruments SSX-100 Small Spot ESCA spectrometer equipped with a low energy electron flood gun used to provide charge neutralization for the electrically non-conductive samples and following the manufacturer's procedures and specifications. The data is acquired using an analyzer pass energy of 150 eV for a survey spectra and 50 eV for high resolution spectra. Elemental compositions are calculated, peak fitting of high resolution spectra are made and angular measurements using tilt stage mountings are provided following the manufacturer's specifications.

Stability: Absorbance and rheological properties are measured for designated test solutions over various periods of time and temperature conditions using the previously described procedures. Freeze-thaw stability is determined for designated test solutions subjected to 3 cycles of freezing at −20° C. overnight followed by thawings, with measurements then taken using the previously described test procedures.

EXAMPLE 1

Preparation of Cationic Polymer and Glycosaminoglycan Combinations

Unless otherwise indicated, aqueous solutions are prepared by adding the designated cationic polymer, glycosaminoglycan and/or other ingredients to distilled water, at the concentrations and using the components as set forth in Table I.

TABLE I

EXAMPLE 1: SAMPLE COMBINATIONS

| Run | Cationic Polymer Type | Cationic Polymer Wt. % | Glycosaminoglycan Type | Glycosaminoglycan Wt. % | Weight Ratio[a] | Surfactant Type | Surfactant Wt. % | Other Ingredients Type | Other Ingredients Wt. % |
|---|---|---|---|---|---|---|---|---|---|
| A | — | — | I | 0.001 | — | — | — | — | — |
| 1-1 | I | 0.01 | I | 0.001 | 10:1 | — | — | — | — |
| 1-2 | I | 0.015 | I | 0.001 | 15:1 | — | — | — | — |
| 1-3 | I | 0.02 | I | 0.001 | 20:1 | — | — | — | — |
| 1-4 | I | 0.025 | I | 0.001 | 25:1 | — | — | — | — |
| 1-5 | I | 0.05 | I | 0.001 | 50:1 | — | — | — | — |
| 1-6 | I | 0.035 | I | 0.001 | 35:1 | — | — | — | — |
| 1-7 | I | 0.050 | I | 0.001 | 50:1 | — | — | — | — |
| 1-8 | I | 0.100 | I | 0.001 | 100:1 | — | — | — | — |
| 1-9 | I | 0.01 | I | 0.001[b] | 10:1 | — | — | — | — |
| B | — | — | I | 0.0005 | — | — | — | — | — |
| 2-1 | I | 0.005 | I | 0.0005 | 10:1 | — | — | — | — |
| 2-2 | I | 0.125 | I | 0.0005 | 25:1 | — | — | — | — |
| 3-C | — | — | I | 0.001 | — | I | 0.0006 | — | — |
| 3-1 | I | 0.01 | I | 0.001 | 10:1 | I | 0.0006 | — | — |
| 3-2 | I | 0.025 | I | 0.001 | 25:1 | I | 0.0006 | — | — |
| 4-C | — | — | I | 0.001 | — | II | 10 | — | — |
| 4-1 | I | 0.01 | I | 0.001 | 10:1 | II | 10 | — | — |
| 4-2 | I | 0.025 | I | 0.001 | 25:1 | II | 10 | — | — |
| 5-1 | II | 0.001 | I | 0.001 | 1:1 | — | — | — | — |
| 5-2 | II | 0.005 | I | 0.001 | 5:1 | — | — | — | — |
| 5-3 | II | 0.009 | I | 0.001 | 9:1 | — | — | — | — |
| 5-4 | II | 0.01 | I | 0.001 | 10:1 | — | — | — | — |
| 5-5 | II | 0.025 | I | 0.001 | 25:1 | — | — | — | — |
| 6-C | — | — | I | 0.001 | — | III | 0.10 | — | — |
| 6-1 | I | 0.01 | I | 0.001 | 10:1 | III | 0.10 | — | — |

TABLE I-continued

EXAMPLE 1: SAMPLE COMBINATIONS

| Run | Cationic Polymer Type | Wt. % | Glycosaminoglycan Type | Wt. % | Weight Ratio[a] | Surfactant Type | Wt. % | Other Ingredients Type | Wt. % |
|---|---|---|---|---|---|---|---|---|---|
| 6-2 | I | 0.025 | I | 0.001 | 25:1 | III | 0.10 | — | |
| 6-3 | I | 0.01 | I | 0.001 | 10:1 | III | 0.002 | — | |
| C | — | | I | 0.01 | — | — | | — | |
| 7-1 | I | 0.2 | I | 0.01 | 20:1[b] | — | | — | |
| 7-2 | I | 0.2 | I | 0.01 | 20:1 | — | | — | |
| 7-3 | I | 0.15 | I | 0.01 | 15:1 | — | | — | |
| 8-1 | I | 0.018 | I | 0.0007 | 25:1 | — | | — | |
| 8-2 | I | 0.018 | I | 0.0007 | 25:1 | I | 0.0003 | — | |
| 8-3 | I | 0.018 | I | 0.0007 | 25:1 | I | 0.0007 | — | |
| 8-4 | I | 0.018 | I | 0.0007 | 25:1 | I | 0.0014 | — | |
| 8-5 | I | 0.018 | I | 0.0007 | 25:1 | I | 0.0036 | — | |
| 8-6 | I | 0.018 | I | 0.0007 | 25:1 | I | 0.0071 | — | |
| 9 | I | 0.018 | I | 0.0007 | 25:1 | — | | API[c] | 0.0007 |
| 10 | I | 0.025 | I | 0.001 | 25:1 | IV | 0.001 | — | |
| 11 | I | 0.025 | I | 0.001 | 25:1 | — | | PI[d] | 0.003 |
| 12 | I | 0.025 | I | 0.001 | 25:1 | I | 0.002 | — | |
| 13 | I | 0.025 | I | 0.001 | 25:1 | — | | Ethanol | 25 |
| 13-2 | I | 0.025 | I | 0.001 | 25:1 | — | | Ethanol 25, NPI[e] | 0.05 |
| 14-1 | I | 0.025 | I | 0.001 | 25:1 | V | 7.5 | — | |
| 14-2 | I | 0.025 | I | 0.001 | 25:1 | V 7.5, I | 0.002 | — | |
| 14-3 | I | 0.025 | I | 0.001 | 25:1 | IV 5, I | 0.002 | — | |
| 15 | I | 0.01 | III | 0.001 | 10:1[b] | — | | — | |
| 16 | I | 0.01 | IV | 0.001 | 10:1[b] | — | | — | |
| D | I | 0.01 | — | | — | — | | — | |
| E | — | | I | 0.0038 | — | — | | — | |
| F | I | 0.095 | — | | — | — | | — | |
| 17-1 | I | 0.095 | I | 0.0038 | 25:1[b] | — | | — | |
| 17-2 | I | 0.095 | I | 0.0038 | 25:1 | — | | — | |
| 18-C | I | 1 | — | | — | — | | — | |
| 18-1 | I | 1 | I | 0.01 | 100:1 | — | | — | |
| 18-2 | I | 1 | I | 0.02 | 50:1 | — | | — | |
| 18-3 | I | 1 | I | 0.03 | 33:1 | — | | — | |
| 18-4 | I | 1 | I | 0.04 | 25:1 | — | | — | |
| 18-5 | I | 1 | I | 0.05 | 20:1 | — | | — | |
| 18-6 | I | 1 | I | 0.06 | 16:1 | — | | — | |
| 18-7 | I | 1 | I | 0.07 | 14:1 | — | | — | |
| 18-8 | I | 1 | I | 0.08 | 12:1 | — | | — | |
| 18-9 | I | 1 | I | 0.09 | 11:1 | — | | — | |
| 18-10 | I | 1 | I | 0.10 | 10:1 | — | | — | |
| 19-C | I | 2 | — | | — | — | | — | |
| 19-1 | I | 2 | I | 0.20 | 100:1 | — | | — | |
| 19-2 | I | 2 | I | 0.04 | 50:1 | — | | — | |
| 19-3 | I | 2 | I | 0.06 | 33:1 | — | | — | |
| 19-4 | I | 2 | I | 0.08 | 25:1 | — | | — | |
| 19-5 | I | 2 | I | 0.10 | 20:1 | — | | — | |
| 19-6 | I | 2 | I | 0.12 | 16:1 | — | | — | |
| 19-7 | I | 2 | I | 0.14 | 14:1 | — | | — | |
| 19-8 | I | 2 | I | 0.16 | 12:1 | — | | — | |
| 19-9 | I | 2 | I | 0.18 | 11:1 | — | | — | |
| 19-10 | I | 2 | I | 0.20 | 10:1 | — | | — | |
| 20-1 | I | 0.2 | I | 0.002 | 100:1 | — | | — | |
| 20-2 | I | 0.2 | I | 0.006 | 33:1 | — | | — | |
| 20-3 | I | 0.2 | I | 0.010 | 20:1 | — | | — | |
| 20-4 | I | 0.2 | I | 0.016 | 12:1 | — | | — | |
| 20-5 | I | 0.2 | I | 0.020 | 10:1 | — | | — | |
| 21-1 | I | 2 | II | 0.02 | 100:1 | — | | — | |
| 21-2 | I | 2 | II | 0.06 | 33:1 | — | | — | |
| 21-3 | I | 2 | II | 0.10 | 20:1 | — | | — | |
| 21-4 | I | 2 | II | 0.12 | 17:1 | — | | — | |
| 21-5 | I | 2 | II | 0.16 | 12:1 | — | | — | |
| 21-6 | I | 2 | II | 0.20 | 10:1 | — | | — | |
| 22-C | I | 0.2 | II | — | — | — | | — | |
| 22-1 | I | 0.2 | II | 0.002 | 100:1 | — | | — | |
| 22-2 | I | 0.2 | II | 0.006 | 33:1 | — | | — | |
| 22-3 | I | 0.2 | II | 0.010 | 20:1 | — | | — | |
| 22-4 | I | 0.2 | II | 0.012 | 17:1 | — | | — | |
| 22-5 | I | 0.2 | II | 0.016 | 12:1 | — | | — | |
| 22-6 | I | 0.2 | II | 0.020 | 10:1 | — | | — | |
| 23-C | II | 2 | — | | — | — | | — | |
| 23-1 | II | 2 | I | 0.02 | 100:1 | — | | — | |
| 23-2 | II | 2 | I | 0.06 | 33:1 | — | | — | |
| 23-3 | II | 2 | I | 0.10 | 20:1 | — | | — | |
| 23-4 | II | 2 | I | 0.14 | 14:1 | — | | — | |
| 23-5 | II | 2 | I | 0.18 | 11:1 | — | | — | |

TABLE I-continued

EXAMPLE 1: SAMPLE COMBINATIONS

| Run | Cationic Polymer Type | Wt. % | Glycosaminoglycan Type | Wt. % | Weight Ratio$^a$ | Surfactant Type | Wt. % | Other Ingredients Type | Wt. % |
|---|---|---|---|---|---|---|---|---|---|
| 23-6 | II | 2 | I | 0.22 | 9:1 | — | — | — | — |
| 23-C' | II | 0.2 | — | — | — | — | — | — | — |
| 23-7 | II | 0.2 | I | 0.002 | 100:1 | — | — | — | — |
| 23-8 | II | 0.2 | I | 0.006 | 33:1 | — | — | — | — |
| 23-9 | II | 0.2 | I | 0.010 | 20:1 | — | — | — | — |
| 23-10 | II | 0.2 | I | 0.014 | 14:1 | — | — | — | — |
| 23-11 | II | 0.2 | I | 0.018 | 11:1 | — | — | — | — |
| 23-12 | II | 0.2 | I | 0.022 | 9:1 | — | — | — | — |
| 24-C | III | 2 | — | — | — | — | — | — | — |
| 24-1 | III | 2 | I | 0.02 | 100:1 | — | — | — | — |
| 24-2 | III | 2 | I | 0.06 | 33:1 | — | — | — | — |
| 24-3 | III | 2 | I | 0.10 | 20:1 | — | — | — | — |
| 24-4 | III | 2 | I | 0.14 | 14:1 | — | — | — | — |
| 24-5 | III | 2 | I | 0.18 | 11:1 | — | — | — | — |
| 24-6 | III | 2 | I | 0.22 | 9:1 | — | — | — | — |
| 24-C' | III | 0.2 | — | — | — | — | — | — | — |
| 24-7 | III | 0.2 | I | 0.002 | 100:1 | — | — | — | — |
| 24-8 | III | 0.2 | I | 0.006 | 33:1 | — | — | — | — |
| 24-9 | III | 0.2 | I | 0.010 | 20:1 | — | — | — | — |
| 24-10 | III | 0.2 | I | 0.014 | 14:1 | — | — | — | — |
| 24-11 | III | 0.2 | I | 0.018 | 11:1 | — | — | — | — |
| 24-12 | III | 0.2 | I | 0.022 | 9:1 | — | — | — | — |
| 25-C | IV | 1 | — | — | — | — | — | — | — |
| 25-1 | IV | 1 | I | 0.02 | 50:1 | — | — | — | — |
| 25-2 | IV | 1 | I | 0.06 | 16:1 | — | — | — | — |
| 25-3 | IV | 1 | I | 0.10 | 10:1 | — | — | — | — |
| 25-4 | IV | 1 | I | 0.14 | 7:1 | — | — | — | — |
| 25-5 | IV | 1 | I | 0.18 | 5.6:1 | — | — | — | — |
| 25-C' | IV | 0.1 | — | — | — | — | — | — | — |
| 25-6 | IV | 0.1 | I | 0.002 | 50:1 | — | — | — | — |
| 25-7 | IV | 0.1 | I | 0.006 | 16:1 | — | — | — | — |
| 25-8 | IV | 0.1 | I | 0.010 | 10:1 | — | — | — | — |
| 25-9 | IV | 0.1 | I | 0.014 | 7:1 | — | — | — | — |
| 25-10 | IV | 0.1 | I | 0.018 | 5.6:1 | — | — | — | — |
| 26 | I | 0.5 | I | various | — | — | — | — | — |
| 27 | I | 1 | I | various | — | — | — | — | — |
| 28 | I | 2 | I | various | — | — | — | — | — |
| 29 | V | 2 | I | various | — | — | — | — | — |
| 30 | VI | 2 | I | various | — | — | — | — | — |
| 31 | VII | 1 | I | various | — | — | — | — | — |
| 32 | VIII | 2 | I | various | — | — | — | — | — |
| 33-1 | I | 2 | I | 0.2 | 10:1 | VI | 0.1 | — | — |
| 33-2 | I | 2 | I | 0.2 | 10:1 | VI | 1.0 | — | — |
| 33-3 | I | 2 | I | 0.2 | 10:1 | VI | 5.0 | — | — |
| 33-4 | I | 0.2 | I | 0.02 | 10:1 | VI | 0.01 | — | — |
| 33-5 | I | 0.2 | I | 0.02 | 10:1 | VI | 0.10 | — | — |
| 33-6 | I | 0.2 | I | 0.02 | 10:1 | VI | 0.50 | — | — |
| 34-1 | I | 2.5 | I | 0.1 | 25:1 | — | — | — | — |
| 34-2 | I | 2.5 | I | 0.1 | 25:1 | V1 | 0.1 | — | — |
| 34-3 | I | 2.5 | I | 0.1 | 25:1 | VI | 1.0 | — | — |
| 34-4 | I | 2.5 | I | 0.1 | 25:1 | VI | 5.0 | — | — |
| 34-5 | I | 0.25 | I | 0.01 | 25:1 | — | — | — | — |
| 34-6 | I | 0.25 | I | 0.01 | 25:1 | VI | 0.01 | — | — |
| 34-7 | I | 0.25 | I | 0.01 | 25:1 | VI | 0.10 | — | — |
| 34-8 | I | 0.25 | I | 0.01 | 25:1 | VI | 0.05 | — | — |
| 35-1 | I | 2 | I | 0.2 | 10:1 | VII | 0.1 | — | — |
| 35-2 | I | 2 | I | 0.2 | 10:1 | VII | 1.0 | — | — |
| 35-3 | I | 2 | I | 0.2 | 10:1 | VII | 5.0 | — | — |
| 35-4 | I | 0.2 | I | 0.02 | 10:1 | VII | 0.01 | — | — |
| 35-5 | I | 0.2 | I | 0.02 | 10:1 | VII | 0.10 | — | — |
| 35-6 | I | 0.2 | I | 0.02 | 10:1 | VII | 0.50 | — | — |
| 36-1 | I | 2.5 | I | 0.1 | 25:1 | VII | 0.1 | — | — |
| 36-2 | I | 2.5 | I | 0.1 | 25:1 | VII | 1.0 | — | — |
| 36-3 | I | 2.5 | I | 0.1 | 25:1 | VII | 5.0 | — | — |
| 36-4 | I | 0.25 | I | 0.01 | 25:1 | VII | 0.01 | — | — |
| 36-5 | I | 0.25 | I | 0.01 | 25:1 | VII | 0.10 | — | — |
| 36-6 | I | 0.25 | I | 0.01 | 25:1 | VII | 0.50 | — | — |
| 37-1 | I | 2 | I | 0.2 | 10:1 | IV | 0.1 | — | — |
| 37-2 | I | 2 | I | 0.2 | 10:1 | IV | 1.0 | — | — |
| 37-3 | I | 2 | I | 0.2 | 10:1 | IV | 5.0 | — | — |
| 37-4 | I | 0.2 | I | 0.02 | 10:1 | IV | 0.01 | — | — |
| 37-5 | I | 0.2 | I | 0.02 | 10:1 | IV | 0.10 | — | — |
| 37-6 | I | 0.2 | I | 0.02 | 10:1 | IV | 0.50 | — | — |
| 38-1 | I | 2.5 | I | 0.1 | 25:1 | IV | 0.1 | — | — |
| 38-2 | I | 2.5 | I | 0.1 | 25:1 | IV | 1.0 | — | — |
| 38-3 | I | 2.5 | I | 0.1 | 25:1 | IV | 5.0 | — | — |
| 38-4 | I | 0.25 | I | 0.01 | 25:1 | IV | 0.01 | — | — |

TABLE I-continued

EXAMPLE 1: SAMPLE COMBINATIONS

| Run | Cationic Polymer Type | Cationic Polymer Wt. % | Glycosaminoglycan Type | Glycosaminoglycan Wt. % | Weight Ratio[a] | Surfactant Type | Surfactant Wt. % | Other Ingredients Type | Other Ingredients Wt. % |
|---|---|---|---|---|---|---|---|---|---|
| 38-5 | I | 0.25 | I | 0.01 | 25:1 | IV | 0.10 | — | |
| 38-6 | I | 0.25 | I | 0.01 | 25:1 | IV | 0.50 | — | |
| 39-1 | I | 0.25 | I | 0.025 | 10:1 | — | | PI[d] | 0.03 |
| 39-2 | I | 0.25 | I | 0.025 | 10:1 | III | 0.4 | PI[d] | 0.03 |
| 39-3 | I | 0.25 | I | 0.025 | 10:1 | III | 1.0 | PI[d] | 0.03 |
| 39-4 | I | 0.25 | I | 0.025 | 10:1 | III | 2.0 | PI[d] | 0.03 |
| 39-5 | I | 0.25 | I | 0.025 | 10:1 | III | 3.0 | PI[d] | 0.03 |
| 39-6 | I | 0.25 | I | 0.025 | 10:1 | III | 4.0 | PI[d] | 0.03 |
| G | — | | I | 0.02 | — | — | | — | |
| H | — | | I | 0.04 | — | — | | — | |
| I | — | | I | 0.1 | — | — | | — | |
| I' | — | | I | 0.1 | — | — | | — | |
| 40-1 | I | 2.0 | I | 0.1 | 20:1 | — | | PI[d] | 0.3 |
| 40-2 | I | 2.0 | I | 0.1 | 20:1 | — | | PII[f] | 0.3 |
| 40-3 | I | 2.5 | I | 0.1 | 25:1 | — | | PI[d] | 0.3 |
| 40-4 | I | 2.5 | I | 0.1 | 25:1 | II | 10 | PI[d] | 0.3 |
| 40-5 | I | 2.5 | II | 0.1 | 25:1 | — | | PI[d] | 0.7 |
| 40-6 | I | 2.5 | II | 0.1 | 25:1 | II | 10 | PI[d] | 0.7 |
| 40-7 | I | 2.5 | I | 0.1 | 25:1 | — | | — | |
| 40-8 | I | 2.5 | I | 0.1 | 25:1 | — | | SI[g] | 0.3 |
| 40-9 | I | 2.5 | I | 0.1 | 25:1 | — | | PI[d] | 0.3 |

Footnotes for Table I:
[a]Relative weight ratio of cationic polymer to glycosaminoglycan.
[b]Cationic polymer applied initially followed by glycosaminoglycan application.
[c]Anionic Polner I as described previously.
[d]Preservative I as described previously.
[e]Nonionic Polymer I as described previously.
[f]Preservative II as described previously.
[g]Solvent I as described previously.

EXAMPLE 2

Personal Care Formulations and Feel

In this example, personal care formulations containing cationic polymer, glycosaminoglycan and other personal care ingredients as listed in Table II are prepared using the following general procedures, unless otherwise indicated. The designated formulation is generally provided by forming the designated oil and water phases, except for the GERMABEN® IIE, Cationic Polymer I and Glycosaminoglycan I, and heating both phases to 85° C. The water phase is added to the oil phase with vigorous stirring. The GERMABEN® IIE, when used, is then added at 75° C. followed by addition of a 0.1% actives aqueous solution of Cationic Polymer I and Glycosaminoglycan I combination, provided at a weight ratio of cationic polymer to glycosaminoglycan of 25:1, which is added to the designated formulation at room temperature with thorough agitation.

Formulation 1: Dry Skin Lotion

A dry skin lotion, containing the concentration of ingredients listed in Formulation 1 of Table II, is prepared following the previously described general procedures except that the magnesium aluminum silicate is initially dispersed as a slurry in water at the designated concentration using high speed mixing.

Formulation 2: Moisturizing Lotion

A moisturizing lotion, containing the concentrations of ingredients noted in Formulation 2 of Table II, is prepared following the previously described general procedures.

Formulation 3: Hand Lotion

A hand lotion, containing the concentrations of ingredients listed in Formulation 3 of Table II, is prepared following the previously described general procedures, except that the oil and water phases are initially heated to 75° C. instead of 85° C.

Formulation 4: Mild Lotion

A mild lotion, containing the concentrations of ingredients listed in Formulation 4 of Table II, is prepared following the previously described general procedures, except that the oil and water phases are initially heated to 75° C. instead of 85° C. and the triethanolamine is added at 75° C. after the water phase is added to the oil phase.

Formulation 5: Enriched Lotion

An enriched lotion, containing the concentrations of ingredients listed in Formulation 5 of Table II, is prepared following the previously described general procedures.

Formulaltion 6: Dry Skin Cream

A dry skin cream, containing the concentrations of ingredients in Formulation 6 of Table II, is prepared as follows. Xanthan gum is dispersed in water with vigorous agitation at 70° C. The magnesium aluminum silicate slurry is formed and heated to 70° C. with vigorous mixing. The oil phase ingredients are combined and heated to 70° C. Both aqueous phases, i.e., xanthan and silicate, are added, one at a time, to the oil phase with vigorous mixing. The GERMABEN® IIE is added followed by the previously described addition of Cationic Polymer I and Glycosaminoglycan I combination.

Formulation 7: Cleansing Cream

A cleansing cream, containing the concentrations of ingredients listed in Formulation 7 of Table II, is prepared following the previously described general procedures except that the oil and water phases are initially heated to 80° C. instead of 85° C.

Formulation 8: Liquid Cream

A liquid cream, containing the concentrations of ingredients listed in Formulation 8 of Table II, is prepared using the previously described general procedures except as follows. The Carbomer 934 is initially dispersed as a slurry in water with high speed agitation. The triethanolamine solution is added after obtaining a uniform mixture of the oil and water phases.

Formulation 9: Moisturizing Cream

A moisturizing cream, containing the concentrations of ingredients listed in Formulation 9 of Table II, is prepared using the previously described general procedures except as follows. The oil and water phases are initially heated to 75° C. instead of 85° C. The Carbomer 934 is initially dispersed as a slurry in water with high speed agitation. The triethanolamine solution is added after obtaining a uniform mixture of the oil and water phases.

Formulation 10: All Purpose Cream

An all purpose cream, containing the concentrations of ingredients listed in Formulation 10 of Table II, is prepared following the previously described general procedures.

Formulation 11: All-Purpose Skin Conditioning Lotion

An all purpose skin conditioning lotion, containing the concentrations of ingredients listed in Formulation 11 of Table II, is prepared following the previously described general procedures except that the Cationic Polymer I and Glycosaminoglycan I combination is added at 40° C. while cooling to 30° C. instead of at room temperature.

Formulation 12: Conditioning and Styling Mousse

A conditioning and styling mousse, containing the concentration of ingredients listed in Formulation 12 of Table II, is prepared by initially combining the ingredients of the water phase with mixing at 75° C. until a uniform composition is obtained, followed by cooling to 40° C. The alcohol phase is subsequently added at room temperature followed by mixing until a uniform composition is obtained. The Cationic Polymer I and Glycosaminoglycan I combination is then added, as generally described previously, with mixing until a uniform composition is obtained. An aerosol composition is obtained by adding an isobutane/propane blend as propellant at a weight ratio of 9:1 of formulation to propellant.

TABLE II

PERSONAL CARE FORMULATION

| Ingredients:[a] (conc. in wt %) | 1 | 2 | 3 | 4 | 5 | 6 | 7 | 8 | 9 | 10 | 11 | 12 |
|---|---|---|---|---|---|---|---|---|---|---|---|---|
| Oil Phase: | | | | | | | | | | | | |
| AMERCHOL ® L-101[b] | 5.0 | | | | | | | 5.0 | | 5.0 | | |
| Petrolatum | 5.0 | | | | | 8.0 | | | | | | |
| Mineral oil[c] | 33.5 | | 4.0 | 5.0 | 25.0 | 6.0 | 44.0[z] | 3.5 | 2.0 | | 2.0 | |
| Lanolin[d] | 3.0 | | | | | | | | | | | |
| Sorbitan sesquioleate | 2.5 | | | | | | | | | | | |
| Beeswax (U.S.P.) 4.0 | | | | | | 10.0 | | | | | | |
| GLUCATE ® SS[e] | 0.5 | | | 0.5 | | | | | 0.5 | | 2.0 | |
| AMERLATE ® P[f] | | 0.5 | | | | | 2.0 | 1.0 | | | | |
| Stearic acid | | 3.0 | | | 3.0 | | | 1.5 | | | | |
| Glyceryl stearate | | 2.0 | 4.0[x] | | 3.0 | | 2.0 | 2.0 | | | | |
| SOLULAN ® 98[g] | | | 2.0 | | | | | | | | | 2.0* |
| SOLULAN ® 5[h] | | | 1.0 | | 0.5 | | | | | | 0.5 | |
| Cetyl alcohol | | | 1.0 | 0.5 | | 1.0 | | | 0.5 | 10.0 | | |
| GLUCAMATE ® SSE-20[i] | | | | 1.5 | | 3.0 | | | 1.5 | | 2.0 | |
| Squalane | | | | 0.9 | | | | | | | | |
| SOLULAN ® C-24[j] | | | | | 0.3 | | | | | | | |
| GLUCATE ® DO[k] | | | | | | 1.5 | | | | | | |
| Isopropyl palmitate | | | | | | 3.0 | | | | | | |
| Stearyl alcohol | | | | | | 2.0 | | | | | | |
| Dimethicone | | | | | | 0.5 | | | | 1.0 | | |
| OHLAN ®[l] | | | | | | | 3.0 | | | | | |
| Ozokerite wax | | | | | | | 5.0 | | | | | |
| GLUCAM ® P-20 distearate[m] | | | | | | | | | 4.0 | | | |
| SOLULAN ® 16[n] | | | | | | | | | | 3.0 | | 1.5* |
| Myristyl myristate | | | | | | | | | | 5.0 | | |
| PROMULGEN ® G[o] | | | | | | | | | | | 5.0 | |
| Water Phase: | | | | | | | | | | | | |
| MgAl silicate[p] | 12.5 | | | | | 25.0 | | | | | | |
| Sodium borate | 0.5 | | | | | 0.6 | | | | | | |
| GLUCAM ® E-20[q] | 2.0 | 5.0 | | | | | | | | | | |
| GERMABEN ® IIE[r] | 1.0 | 1.0 | 1.0 | 1.0 | 1.0 | 1.0 | 1.0 | 1.0 | 1.0 | 1.0 | | |
| Triethanolamine | | 1.0 | | 3.0[y] | 1.0 | | | 10.0[y] | 3.0[y] | | | |
| Steapyrium chloride | | | 0.1 | | | | | | | | | |
| Glycerin | | | 2.0 | | | | | | | | 2.5 | |
| Carbomer 934[s] | | | | 10.0 | | | | 10.0 | 10.0 | | | |
| Propylene glycol | | | | | 4.0 | | | | 5.0 | | | |
| Xanthan gum | | | | | | 0.3 | | | | | | |
| Methylbenzethonium chloride | | | | | | | | | | | 0.1 | |
| GLUCAM ® E-10[t] | | | | | | | | | | | 3.5 | |
| GLUCAM ® P-10[u] | | | | | | | | | | | | 1.5 |
| Cationic Polymer I | 0.0962 | 0.0962 | 0.0962 | 0.0962 | 0.0962 | 0.0962 | 0.0962 | 0.0962 | 0.0962 | 0.0962 | 0.0962 | 0.125 |
| Glycosaminoglycan I | 0.0038 | 0.0038 | 0.0038 | 0.0038 | 0.0038 | 0.0038 | 0.0038 | 0.0038 | 0.0038 | 0.0038 | 0.0038 | 0.005 |
| Water | q.s | q.s | q.s | q.s | q.s | q.s | q.s | q.s | q.s | q.s | q.s | 73.0 |
| Alcohol Phase: | | | | | | | | | | | | |

TABLE II-continued

PERSONAL CARE FORMULATION

| Ingredients:[a] (conc. in wt %) | 1 | 2 | 3 | 4 | 5 | 6 | 7 | 8 | 9 | 10 | 11 | 12 |
|---|---|---|---|---|---|---|---|---|---|---|---|---|
| Ethyl alcohol[v] | | | | | | | | | | | | 15.0 |
| AMERSETTE ® resin[w] | | | | | | | | | | | | 2.0 |

Footnotes for Table II:
[a]Unless otherwise indicated all trademark ingredients are available from Amerchol Corp.
[b]Blend of mineral oil and fraction of lanolin alcohol.
[c]70 SSU viscosity.
[d]Anhydrous lanolin U.S.P., deoderized AAA.
[e]Methyl glucose sesquistearate.
[f]Isopropyl lanolate.
[g]Blend of polysorbate-80, cetyl acetate and acetylated lanolin alcohol.
[h]Blend of laneth-5, ceteth-5, oleth-5 and steareth-5.
[i]PEG-20 methyl glucose sesquistearate.
[j]Blend of choleth-24 and ceteth-24.
[k]Methyl glucose dioleate.
[l]Hydroxylated lanolin.
[m]PPG-20 methyl glucose ether distearate.
[n]Blend of laneth-16, ceteth-16, oleth-16 and steareth-16.
[o]Blend of stearyl alcohol and ceteareth-20.
[p]4% aqueous solution of magnesium aluminum silicate.
[q]Methyl gluceth-20.
[r]Blend of propylene glycol, diazolidinyl urea, methylparaben and propylparaben, available from Sutton Laboratories.
[s]3% aqueous solution of crosslinked polyacrylic acid.
[t]Methyl gluceth-10.
[u]PPG-10 methyl glucose ether.
[v]Specially denatured, #40.
[w]Copolymer of methacrylol ethyl betaine and methacrylates.
[x]Blend of glyceryl stearate and PEG-100 stearate.
[y]10% aqueous solution.
[z]80-90 SSU viscosity.
*Provided in water phase (no oil phase).

Using the previously described procedures, the feel of each formulation is evaluated as providing superior afterfeel properties. These formulations provide comparable feel and afterfeel properties to identical formulations except which contain 0.05 wt. % Glycosaminoglycan I in place of the designated cationic polymer and glycosaminoglycan combinations. Comparable feel properties are not provided by equivalent formulations containing an equal or greater concentration of the designated cationic polymer only. These results demonstrate that low concentrations of glycosaminoglycan, when combined with the designated cationic polymer, exhibit superior feel properties comparable to the properties provided by much higher concentrations of glycosaminoglycan when no cationic polymer is present.

EXAMPLES 3-4

Hair Treatment and Substantivity

EXAMPLE 3

Hair Substantivity Using Radiolabelled Glycosaminoglycan.

In this example the substantivity of the designated test solutions, using radiolabelled glycosaminoglycan, is evaluated using the previously described procedures with the results set forth in Table III.

TABLE III

EXAMPLE 3: HAIR SUBSTANTIVITY MEASUREMENTS USING RADIOLABELLED GLYCOSAMINOGLYCAN

| Test No. | Run No. | Amount of Bound Glycosaminoglycan (% DPM*) |
|---|---|---|
| 1 | A | 17/13 |
| 2 | 1-1 | 64/79 |
| 3 | 1-2 | 15/— |
| 4 | 1-3 | 9/— |
| 5 | 1-4 | 7/10 |
| 6 | 1-5 | —/5 |
| 7 | 3-C | 9 |
| 8 | 3-1 | 53 |
| 9 | 3-2 | 8 |
| 10 | 4-C | 2 |
| 11 | 4-1 | 12 |
| 12 | 4-2 | 3 |
| 13 | A | 22 |
| 14 | 5-1 | 20 |
| 15 | 5-2 | 34 |
| 16 | 5-3 | 24 |
| 17 | 5-4 | 15 |
| 18 | 5-5 | 5 |
| 19 | A | 16 |
| 20 | 1-1 | 49 |
| 21 | 1-4 | 7 |
| 22 | 6-C | 0.2 |
| 23 | 6-1 | 1 |
| 24 | 6-2 | 1 |
| 25 | 6-3 | 52 |
| 26 | A | 17 |
| 27 | 1-3 | 9 |
| 28 | 1-2 | 15 |
| 29 | 1-1 | 62 |
| 30 | C | 2 |
| 31 | 7-1 | 6 |
| 32 | 7-2 | 1 |
| 33 | 7-3 | 2 |
| 34 | 8-1 | 11 |
| 35 | 8-2 | 22 |
| 36 | 8-3 | 40 |
| 37 | 8-4 | 35 |
| 38 | 8-5 | 37 |
| 39 | 8-6 | 6 |
| 40 | 8-1 | 11 |
| 41 | 9 | 54 |
| 42 | 1-4 | 10 |
| 43 | 10 | 6 |
| 44 | 11 | 10 |
| 45 | 1-4 | 9 |
| 46 | 12 | 61 |
| 47 | 13-1 | 8 |
| 48 | 13-2 | 10 |

TABLE III-continued

EXAMPLE 3: HAIR SUBSTANTIVITY MEASUREMENTS
USING RADIOLABELLED GLYCOSAMINOGLYCAN

| Test No. | Run No. | Amount of Bound Glycosaminoglycan (% DPM*) |
|---|---|---|
| 49 | 14-1 | 0.2 |
| 50 | 14-2 | 0.1 |
| 51 | 14-3 | 25 |

*disintegrations per minute.

The results in Table III demonstrate that improved substantivity of the glycosaminoglycan to hair is provided by various cationic polymers and glycosaminoglycan combinations. The presence and extent of such substantivity is also effected by the relative proportions of cationic polymer and glycosaminoglycan and application procedures as well as the type and amount of surfactants or other optional ingredients provided. In an embodiment where the cationic polymer is applied separately and before the glycosaminoglycan, the substantivity of the glycosaminoglycan is substantially enhanced.

EXAMPLE 4

Hair Substantivity Using Electrokinetic Streaming Potential

In this example, the substantivity of glycosaminoglycan to hair is evaluated using the previously described electrokinetic streaming potential procedures, with the results set forth in Table IV. The tests are conducted using treating solutions described by the designated run, in Step 1 as described previously, and $10^{-4}$ N $KNO_3$ measuring solution, in Step 3 as described previously, except for the sequential polymer applications in Test Nos. 3 through 5 where the cationic polymer solution is used as the treating solution (in Step 1) followed by the glycosaminoglycan solution as the measuring solution (in Step 3).

TABLE IV

EXAMPLE 4: HAIR SUBSTANTIVITY MEASUREMENTS
USING ELECTROKINETIC STREAMING POTENTIAL

| Test No. | Run No. | Zeta Potential (millivolts) | | |
|---|---|---|---|---|
| | | 0 min. | 15 mins. | 60 min. |
| 1 | — | −35* | −35* | −35* |
| 2 | D | +11 | +6 | +3 |
| 3 | 1-9 | +6 | −11 | −16 |
| 4 | 15 | +5 | −8 | −6 |
| 5 | 16 | +3 | −5 | −7 |
| 6 | 1-1 | +6 | +6 | +3 |
| 7 | A | −40 | −40 | −40 |

*Average of values varying between −30 and −40 mV

Test No. 2 reveals that Cationic Polymer I, a cationic polyelectrolyte, is adsorbed onto hair, changing its normally negative potential to positive, and that it is strongly retained since the potential remains positive over an hour's period in contact with a polymer-free solution, of $10^{-4}$ N $KNO_3$.

Tests Nos. 3 through 5, representing the sequential treatment made, strongly indicate that the negatively charged glycosominoglycans of hyaluronic acid, heparin and chondroitin sulfate, adsorb onto the Cationic Polymer I treated hair since in all three cases they transform the positive potential of hair so treated with a polycation to a negative potential. In the absence of the polycation, none of these negatively charged polyions would be expected to adsorb on the negatively charged hair, as confirmed by the results of Test No. 7.

Test No. 6, representing the co-treatment mode, provides information indicating that the glycosaminoglycan is adsorbed onto hair under the conditions of this experiment, i.e. when it is present with a tenfold excess of Cationic Polymer I. The latter is expected to be strongly adsorbed to the hair and convert its charge from negative to positive. When this occurs there will be a strong attraction for the polyanion glycosaminoglycan which, however, being present in lesser amount is insufficient to again reverse the charge, i.e. from positive to negative.

EXAMPLES 5-6

Skin Treatment and Substantivity

EXAMPLE 5

Skin Substantivity Using Radiolabelled Glycosaminoglycan

In this example the skin substantivity is measured for various cationic polymer and glycosaminoglycan combinations, using the previously described general procedures for radioactive analysis unless otherwise indicated, with the results as set forth in Table V.

TABLE V

EXAMPLE 5: SKIN SUBSTANTIVITY MEASUREMENTS
USING RADIOLABELLED GLYCOSAMINOGLYCAN

| Test No. | Run No. | Skin Sample (mg) | Amount of Glycosaminoglycan (μg) | |
|---|---|---|---|---|
| | | | Provided | Bound |
| 1 | A | 50 | 40 | 0.58 |
| 2 | 1-1 | 50 | 40 | 0.79 |
| 3 | 1-4 | 50 | 40 | 2.71 |
| 4 | B | 50 | 20 | 0.20 |
| 5 | 2-1 | 50 | 20 | 0.28 |
| 6 | 2-2 | 50 | 20 | 0.51 |
| 7 | A | 100 | 80 | 1.45 |
| 8 | 1-2 | 100 | 80 | 2.63 |
| 9 | 1-4 | 100 | 80 | 6.17 |
| 10 | 1-6 | 100 | 80 | 11.56 |
| 11 | A | 100 | 80 | 1.15 |
| 12 | 1-6 | 100 | 80 | 9.92 |
| 13 | 1-7 | 100 | 80 | 17.53 |
| 14 | 1-8 | 100 | 80 | 9.71 |

The results in Table V demonstrate that substantivity of the glycosaminoglycan to skin is provided by various cationic polymer and glycosaminoglycan combinations, with enhanced substantivity provided, depending upon the amount of cationic polymer and glycosaminoglycan used, as well as the relative proportions thereof.

EXAMPLE 6

Skin Substantivity Measurements Using Electron Spectroscopy

In this example skin substantivity is determined using electron spectroscopy and the previously described general procedures unless otherwise indicated. Substantivity of glycosaminoglycan, the cationic polymer and combinations thereof using either sequential, in Test No. 4, or simultaneous, in Test No. 5, applications of the combination is evaluated and compared with untreated sample, in Test No. 1, as well as with sample treated with only the glycosaminoglycan, in Test No. 2, or cationic polymer, in Test No. 3, with the results set forth in Tables VIA and VIB.

TABLE VIA

EXAMPLE 6: SKIN SUBSTANTIVITY MEASUREMENTS USING ELECTRON SPECTROSCOPY

| Test No. | Run No. | Surface Composition (wt. %)[a] | | | C—O Carbon | N+ Nitrogen | N/N+ Ratio |
|---|---|---|---|---|---|---|---|
| | | C | O | N | | | |
| 1 | Control | 83.8 | 11.4 | 3.1 | — | — | — |
| 2 | E | 82.5 | 11.8 | 3.9 | 10.7 | 0 | NA[c] |
| 3 | F[b] | — | — | — | 19.8 | 0.4 | 2.0 |
| 4 | 17-1 | 81.2 | 16.0 | 1.8 | 18.9 | 0.2 | 5.0 |
| 5 | 17-2 | 80.8 | 18.0 | 0.5 | 21.9 | 0.2 | 2.9 |

[a]Excluding trace residues of S, P, Si and F impurities.
[b]Based on skin sample prepared under similar conditions using a 0.1 wt.% aqueous solution of Cationic Polymer I.
[c]Not applicable, no N+ detected.

The results in Table VIA demonstrate that the cationic polymer and glycosaminoglycan combinations, in contrast to the glycosaminoglycan sample, are deposited onto the skin as shown by increase in surface oxygen content and decrease in surface nitrogen content, characteristic of polysaccharide deposition. The decrease in the level of quaternary nitrogen provided by the cationic polymer and glycosaminoglycan combinations as compared to the cationic polymer alone, despite very similar levels of C—O carbon content, indicates the presence of the glycosaminoglycan, which contains no quaternary nitrogen, along with the cationic polymer containing quaternary nitrogen. The increase in N/N+ ratio, in comparing the cationic polymer and glycosaminoglycan combinations with the cationic polymer only, provides further indication of glycosaminoglycan providing increased nitrogen content free of quaternary nitrogen. Enhanced glycosaminoglycan deposition is provided by the sequential application as compared to the simultaneous application, shown by the increase in N/N+ ratio indicating the presence of additional glycosaminoglycan on the surface.

Measurement of various depths of surface deposition are provided in Table VIB using angular resolved electron spectroscopy analysis, with the results set forth in Table VIB.

TABLE VIB

EXAMPLE 6: SKIN SUBSTANTIVITY MEASUREMENTS DEPTH ANALYSIS USING ELECTRON SPECTROSCOPY

| Test No. | Run No. | N/N+ Ratio at $\theta^{\circ a}$ | | |
|---|---|---|---|---|
| | | 78°(56Å) | 38°(35Å) | 18°(18Å) |
| 6 | 17-1 | 6.2 | 6.4 | 7.2 |
| 7 | 17-2 | 3.2 | 3.3 | 3.4 |

[a]Calculated depth into surface, in angstroms (Å), given for designated angle, ($\theta$), between sample surface and photoelectron analyzer acceptance optics.

The results in Table VIB show increased glycosaminoglycan deposition on the surface, for the sample of sequential application of cationic polymer followed by glycosaminoglycan, as demonstrated by the increase in N/N+ ratio at the designated sampling depths, as compared to the consistent deposition ratio provided by the sample applied simultaneously.

EXAMPLE 7

Compatibility

In this example the compatibility of various cationic polymer and glycosaminoglycan combinations, varying in relative proportions, with or without additional surfactant or other ingredients, is analyzed using the previously described general procedures unless otherwise indicated, with the results set forth in Tables VIIA and VIIB.

TABLE VIIA

EXAMPLE 7: COMPATIBILITY MEASUREMENTS

| Test No. | Run No. | Absorbance | |
|---|---|---|---|
| | | Initial | After ( ) days |
| 1 | 18-C | 0.007 | — |
| 2 | 18-1 | 0.018 | 0.018(11) |
| 3 | 18-2 | 0.051 | — |
| 4 | 18-3 | 0.070 | 0.057(10) |
| 5 | 18-4 | 0.109 | — |
| 6 | 18-5 | 0.201 | 0.157(9) |
| 7 | 18-6 | 0.232 | 0.224(9) |
| 8 | 18-7 | 0.482 | 0.619(9) |
| 9 | 18-8 | 0.731 | 0.959(9) |
| 10 | 18-9 | 1.004 | 1.061(9) |
| 11 | 18-10 | 1.137 | 0.989(9) |
| 12 | 19-C | 0.015 | 0.011(9) |
| 13 | 19-1 | 0.041 | 0.035(9) |
| 14 | 19-2 | 0.069 | 0.066(9) |
| 15 | 19-3 | 0.118 | 0.108(9) |
| 16 | 19-4 | 0.191 | 0.214(9) |
| 17 | 19-5 | 0.416 | 0.474(9) |
| 18 | 19-6 | 0.700 | 0.632(9) |
| 19 | 19-7 | — | — |
| 20 | 19-8 | 1.113 | 0.729(9) |
| 21 | 19-9 | — | — |
| 22 | 19-10 | 1.198 | 0.719(9) |
| 23 | 20-1 | 0.005 | — |
| 24 | 20-2 | 0.021 | — |
| 25 | 20-3 | 0.091 | — |
| 26 | 20-4 | 0.023[a] | — |
| 27 | 20-5 | 0.000[a] | — |
| 28 | 19-C | 0.011 | 0.006(1) |
| 29 | 21-1 | 0.705 | 0.705(1) |
| 30 | 21-2 | 1.673 | 1.670(1) |
| 31 | 21-3 | 2.152 | 2.156(1) |
| 32 | 21-4 | 2.260 | 2.265(1) |
| 33 | 21-5 | 2.379 | 2.376(1) |
| 34 | 21-6 | 2.455 | 2.446(1) |
| 35 | 22-C | 0.003 | −0.005(1) |
| 36 | 22-1 | 0.096 | 0.070(1) |
| 37 | 22-2 | 0.283 | 0.255(1) |
| 38 | 22-3 | 0.563 | 0.549(1) |
| 39 | 22-4 | 0.713 | 0.552(1) |
| 40 | 22-5 | 0.754 | 0.177(1)[b] |
| 41 | 22-6 | 0.991 | 0.010(1)[b] |
| 42 | 23-C | 0.017 | 0.020(1) |
| 43 | 23-1 | 0.038 | 0.039(1) |
| 44 | 23-2 | 0.055 | 0.054(1) |
| 45 | 23-3 | 0.076 | 0.074(1) |
| 46 | 23-4 | 0.084 | 0.098(1) |
| 47 | 23-5 | 0.103 | 0.124(1) |
| 48 | 23-6 | 0.111 | 0.146(1) |
| 49 | 23-C' | 0.002 | 0.002(1) |
| 50 | 23-7 | 0.005 | 0.005(1) |
| 51 | 23-8 | 0.015 | 0.012(1) |
| 52 | 23-9 | 0.026 | 0.019(1) |
| 53 | 23-10 | 0.035 | 0.029(1) |
| 54 | 23-11 | 0.049 | 0.046(1) |
| 55 | 23-12 | 0.066 | 0.057(1) |
| 56 | 24-C | 0.010 | 0.012(1) |
| 57 | 24-1 | 0.458 | 0.480(1) |
| 58 | 24-2 | 0.852 | 0.856(1) |
| 59 | 24-3 | 1.137 | 1.142(1) |
| 60 | 24-4 | 1.347 | 1,345(1) |
| 61 | 24-5 | 1.469 | 1.468(1) |
| 62 | 24-6 | 1.495 | 1,503(1) |
| 63 | 24-C' | 0.002 | 0.003(1) |
| 64 | 24-7 | 0.053 | 0.032(1) |
| 65 | 24-8 | 0.113 | 0.091(1) |
| 66 | 24-9 | 0.163 | 0.148(1) |
| 67 | 24-10 | 0.213 | 0.200(1) |
| 68 | 24-11 | 0.239 | 0.219(1) |
| 69 | 24-12 | 0.255 | 0.233(1) |
| 70 | 25-C | 0.017 | 0.010(3) |
| 71 | 25-1 | 0.179 | 0.199(3) |
| 72 | 25-2 | 0.445 | 0.466(3) |
| 73 | 25-3 | 0.772 | 0.748(3) |
| 74 | 25-4 | 0.946 | 0.936(3) |
| 75 | 25-5 | 1.146 | 1.046(3) |
| 76 | 25-C' | 0.001 | 0.000(3) |

TABLE VIIA-continued

EXAMPLE 7: COMPATIBILITY MEASUREMENTS

| Test No. | Run No. | Absorbance Initial | After ( ) days |
|---|---|---|---|
| 77 | 25-6 | 0.018 | 0.015(3) |
| 78 | 25-7 | 0.042 | 0.041(3) |
| 79 | 25-8 | 0.100 | 0.086(3) |
| 80 | 25-9 | 0.149 | 0.096(3) |
| 81 | 25-10 | 0.217 | 0.108(3) |
| 82 | 19-10 | 0.926 | 0.861(1) |
| 83 | 33-1 | 0.921 | 0.801(1) |
| 84 | 33-2 | 0.792 | 0.674(1) |
| 85 | 33-3 | 0.067 | 0.098(1) |
| 86 | 20-5 | 0.214 | −0.006(1)[a] |
| 87 | 33-4 | 0.304 | 0.015(1)[a] |
| 88 | 33-5 | 0.352 | 0.011(1)[a] |
| 89 | 33-6 | 0.376 | 0.007(1)[a] |
| 90 | 34-1 | 0.173 | 0.242(1) |
| 91 | 34-2 | 0.271 | 0.362(1) |
| 92 | 34-3 | 0.803 | 0.747(1) |
| 93 | 34-4 | 0.225 | 0.157(1) |
| 94 | 34-5 | 0.040 | 0.029(1) |
| 95 | 34-6 | 0.043 | 0.033(1) |
| 96 | 34-7 | 0.169 | 0.118(1) |
| 97 | 34-8 | 0.400 | 0.442(1) |
| 98 | 19-10 | 1.016 | 0.891(1) |
| 99 | 35-1 | 1.062 | 0.905(1) |
| 100 | 35-2 | 1.102 | 0.866(1) |
| 101 | 35-3 | 0.075 | 0.073(1) |
| 102 | 20-5 | 0.298 | 0.020(1)[a] |
| 103 | 35-4 | 0.358 | 0.000(1)[a] |
| 104 | 35-5 | 0.499 | −0.003(1)[a] |
| 105 | 35-6 | 0.527 | 0.012(1)[a] |
| 106 | 34-1 | 0.218 | 0.251(1) |
| 107 | 36-1 | 0.300 | 0.395(1) |
| 108 | 36-2 | 1.045 | 0.941(1) |
| 109 | 36-3 | 0.217 | 0.165(1) |
| 110 | 34-5 | 0.043 | 0.037(1) |
| 111 | 36-4 | 0.045 | 0.026(1) |
| 112 | 36-5 | 0.217 | 0.130(1) |
| 113 | 36-6 | 0.485 | 0.620(1) |
| 114 | 19-10 | 0.937 | 0.854(1) |
| 115 | 37-1 | 0.958 | 0.843(1) |
| 116 | 37-2 | 0.593 | 0.486(1) |
| 117 | 37-3 | 0.028 | 0.030(1) |
| 118 | 20-5 | 0.235 | 0.030(1)[a] |
| 119 | 37-4 | 0.257 | 0.008(1)[a] |
| 120 | 37-5 | 0.282 | 0.020(1)[a] |
| 121 | 37-6 | 0.229 | 0.016(1)[a] |
| 122 | 34-1 | 0.231 | 0.289(1) |
| 123 | 38-1 | 0.420 | 0.523(1) |
| 124 | 38-2 | 0.606 | 0.462(1) |
| 125 | 38-3 | 0.025 | 0.024(1) |
| 126 | 34-5 | 0.050 | 0.048(1) |
| 127 | 38-4 | 0.059 | 0.035(1) |
| 128 | 38-5 | 0.171 | 0.135(1) |
| 129 | 38-6 | 0.321 | 0.375(1) |

[a] visible coacervate
[b] visible precipitate

TABLE VIIB

EXAMPLE 7: COMPATIBILITY OBSERVATIONS

| Test No. | Run No. | Visual Appearance | Ease of Mixing | Compatibility |
|---|---|---|---|---|
| 130 | 26 | Opalescent | Excellent | Excellent |
| 131 | 27 | Opalescent | Excellent | Excellent |
| 132 | 28 | Opalescent | Excellent | Excellent |
| 133 | 29 | Precipitate | Poor | No |
| 134 | 30 | Precipitate | Poor | No |
| 135 | 31 | Precipitate | Poor | No |
| 136 | 32 | Precipitate | Poor | No |
| 137 | 39-1 | Coacervate | — | Good |
| 138 | 39-2 | Coacervate | — | Good |
| 139 | 39-3 | Coacervate | — | Good |
| 140 | 39-4 | Coacervate | — | Good |
| 141 | 39-5 | Clear | — | Excellent |
| 142 | 39-6 | Clear | — | Excellent |

The results in Tables VIIA and VIIB demonstrate that various cationic polymer and glycosaminoglycan combinations, generally depending upon the relative weight ratio of cationic polymer to glycosaminoglycan, provide compatible compositions. The degree of compatibility depends upon not only the type and amount of cationic polymer and glycosaminoglycan provided, but upon the presence and amount of surfactants and other optional ingredients. Particularly desirable compatible combinations are provided using Cationic Polymers I, II, III and IV in combination with Glycosaminoglycan I, as well as such combinations with Preservative I.

EXAMPLE 8

Rheology

In this example, the shear viscosity and modulus of elasticity are measured for various cationic polymer and glycosaminoglycan combinations, using the previously described procedures unless otherwise indicated, with the results as set forth in Table VIII. In Test Nos. 8 through 11 the measured viscosity and elasticity values are compared with calculated values which are the sum of the corresponding values of the same concentration and type of cationic polymer and glycosaminoglycan measured in separate solutions. Test No. 8 is therefore compared with Test Nos. 3 and 7. Test No. 9 is therefore compared with Test Nos. 1 and 4. Test No. 10 is therefore compared with Test Nos. 1 and 5. Test No. 11 is therefore compared with Test Nos. 2 and 6. The degree of enhanced rheology is presented in the ratio of the measured value of the cationic polymer and glycosaminoglycan combination over the calculated value.

TABLE VIII

EXAMPLE 8: SHEAR VISCOSITY AND ELASTICITY MODULUS MEASUREMENTS

| Test No. | Run No. | Shear Viscosity (pascals) at Various Shear Rates ($s^{-1}$) | | | | Modulus of Elasticity ($G^1$, pascals) at Various Frequencies (Hz) | | |
|---|---|---|---|---|---|---|---|---|
| | | 0.19 | 4.6 | 46.5 | 100 | 5.0 | 0.5 | 0.1 |
| 1 | 18-C | — | — | 0.0230 | 0.0224 | 0.294 | 0.0704 | — |
| 2 | 19-C | $1.27^b$ | 0.256 | 0.224 | 0.209 | 1.54 | 0.152 | — |
| 3 | 23-C | 0.700 | 0.517 | — | — | 3.35 | 0.327 | 0.103 |
| 4 | G | — | 0.0318 | 0.00973 | 0.00748 | 0.581 | 0.155 | — |
| 5 | H | — | 0.0678 | 0.0177 | 0.0138 | 0.876 | 0.275 | — |
| 6 | I | $2.02^b$ | 0.178 | 0.0416 | 0.0307 | 1.59 | 0.565 | — |
| 7 | I' | 1.95 | 0.248 | $0.068^e$ | 0.052 | 2.63 | 1.10 | 0.539 |
| 8 | 23-3 | 45.3 | 6.94 | $1.75^e$ | 1.28 | 39.8 | 14.3 | 7.06 |
| | (Calculated) | 2.65 | 0.765 | — | — | 5.98 | 1.427 | 0.642 |
| | Ratio[a] | 17.1 | 9.1 | — | — | 6.6 | 10.0 | 11.0 |
| 9 | 18-2 | $2.41^b$ | 0.239 | 0.0785 | 0.0589 | 1.24 | 0.451 | $0.105^f$ |
| | (Calculated) | — | — | 0.003 | 0.0299 | 0.875 | 0.2245 | — |

TABLE VIII-continued
EXAMPLE 8: SHEAR VISCOSITY AND ELASTICITY MODULUS MEASUREMENTS

| Test No. | Run No. | Shear Viscosity (pascals) at Various Shear Rates ($s^{-1}$) | | | | Modulus of Elasticity ($G^1$, pascals) at Various Frequencies (Hz) | | |
|---|---|---|---|---|---|---|---|---|
| | | 0.19 | 4.6 | 46.5 | 100 | 5.0 | 0.5 | 0.1 |
| | Ratio[a] | — | — | 2.39 | 1.97 | 1.42 | 2.0 | — |
| 10 | 18-4 | 6.99[b] | 0.716 | 0.141 | 0.097 | 2.35 | 0.852 | 0.200[f] |
| | (Calculated) | — | — | 0.0407 | 0.0362 | 1.17 | 0.3454 | — |
| | Ratio[a] | — | — | 3.46 | 1.97 | 2.0 | 2.47 | — |
| 11 | 19-5 | 33.1[b] | 3.08 | 0.763 | 0.555 | 16.2 | 6.91 | — |
| | (Calculated) | 3.29[b] | 0.443 | 0.2656 | 0.2397 | 3.13 | 0.717 | — |
| | Ratio[a] | 10.06[b] | 6.95 | 2.87 | 2.32 | 5.18 | 7.63 | — |
| 12 | 40-1 | +57%[c] | −26%[c] | +18%[c] | +19%[c] | +79%[c] | +135%[c] | — |
| 13 | 40-2 | −34%[c] | −11%[c] | −12%[c] | −11%[c] | −22%[c] | −26%[c] | — |
| 14 | 40-3 | 77.0 | 9.61 | 1.94[e] | 1.36 | 60.3 | — | 20.6 |
| 15 | 40-4 | −87%[d] | −63%[d] | −16%[d] | −2%[d] | −60%[d] | — | −94%[d] |
| 16 | 40-5 | 13.0 | 1.13 | 0.440[e] | 0.349 | 19.7 | — | 9.57 |
| 17 | 40-6 | +30%[d] | +309%[d] | +367%[d] | +367%[d] | +83%[d] | — | −69%[d] |
| 18 | 40-7 | 60.0 | 7.87 | 1.66[e] | 0.95 | 43.9 | 20.0 | 9.90 |
| 19 | 40-8 | 75.3 | 8.43 | 1.74[e] | 0.95 | 48.7 | 25.3 | 14.4 |
| 20 | 40-9 | 77.0 | 9.61 | 1.94[e] | 1.36 | 60.3 | — | 20.6 |

[a]Ratio of measured valve over calculated value.
[b]Based on 0.05 $s^{-1}$ shear rate.
[c]Percent change from measurements of samples without preservative.
[d]Percent change from measurements of samples without surfactant.
[e]Based on 46.2 $s^{-1}$ shear rate.
[f]Based on 0.01 Hz.

The results in Table VIII demonstrate that cationic polymer and glycosaminoglycan combinations generally provide a substantial enhancement in both viscosity and elasticity beyond that which would be predicted through the sum of the viscosity or elasticity values of the cationic polymer and glycosaminoglycan independently. This synergistic enhancement is provided for a wide variety of cationic polymer and glycosaminoglycan combinations, and over a range of relative weight ratios thereof, as well as in combination with select surfactants and other optional ingredients. In one embodiment, a maximum increase in shear viscosity enhancement is provided over a range of from about 25:1 to about 35:1 of cationic polymer to glycosaminoglycan. In another embodiment, the greatest enhancement in elasticity is provided at relative weight ratios of less than about 25:1 of cationic polymer to glycosaminoglycan.

EXAMPLE 9

Stability

In this Example the storage stability and freeze-thaw stability of various cationic polymer and glycosaminoglycan combinations are evaluated, using the previously described general procedures unless otherwise indicated, with the results set forth in Table IX.

TABLE IX
EXAMPLE 9: STABILITY MEASUREMENTS

| Test No. | Run No. | Absorbance, % change | Shear Viscosity at 0.19 $s^{-1}$ in pascals or % change | Modulus of Elasticity at 5.0 Hz in pascals or % change | Storage Conditions | |
|---|---|---|---|---|---|---|
| | | | | | Time, days | Temperature, °C. |
| 1 | 40-3 | −5% | −14.8% | +6.5% | 8 | 20°-25° |
| 2 | 40-3 | +41% | −35.2% | −25.9% | 8 | 50° |
| 3 | 19-5 | +36% | −60% | −11% | 28 | 4° |
| 4 | 40-3 | Unchanged | −4.7% | +9.7% | 28 | 4° |
| 5 | 40-4 | Unchanged | +7.9% | +18.9% | 28 | 4° |
| 6 | 40-5 | Unchanged | −20% | −16.6% | 28 | 4° |
| 7 | 40-3 | +32% | −33% | — | 43 | 20°-25° |
| 8 | 40-3 | +35% | −51% | — | 43 | 50° |
| 9 | 40-3 | +31% | −10% | — | 64 | 4° |
| 10 | 40-3 | +95% | −30% | — | 120 | 20°-25° |
| 11 | 40-3 | Precipitation | — | — | 120 | 50° |
| 12 | 40-3 | +53% | −25 | — | 135 | 4° |
| 13 | 40-3[a] | | | | | |
| | Before: | | 72.4 | 52.8 | | |
| | After: | | 97.3 | 60.8 | | |
| | % Change: | | +34% | +15% | | |

[a]Freeze-thaw analysis based on measurements taken before and after treatment.

The results in Table IX demonstrate that various cationic polymer and glycosaminoglycan combinations, particularly in the presence of preservative, remain stable and compatible compositions, depending upon storage temperature and duration. The presence and amount of surfactant or other optional ingredients can also effect the degree of stability.

We claim:
1. A combination comprising:
   (1) glycosaminoglycan; and

(2) cationic polymer selected from the group consisting water-soluble of cationic derivatives of cellulose ethers, galactomannan, homo- and copolymers of ethylenically unsaturated compounds and poly(N-acylalkyleneimines);

which combination provides modification of the glycosaminoglycan properties due to the presence of the cationic polymer.

2. The combination of claim 1 wherein the glycosaminoglycan is hyaluronan, hylan or other hyaluronan derivative.

3. The combination of claim 2 wherein the glycosaminoglycan is an acid or salt of hyaluronan, hylan or other hyaluronan derivative, a mixture of hyaluronan with proteins and naturally occurring substances derived by the production of hyaluronan from natural material, or mixtures of such materials.

4. The combination of claim 3 wherein the glycosaminoglycan is an alkali metal or alkaline earth metal salt of hyaluronan, hylan or other hyaluronan derivative.

5. The combination of claim 1 wherein the cationic polymer is a cellulose ether represented by the overall structural formula:

$$\begin{bmatrix} R_1 & R_2 & R_3 \\ | & | & | \\ O & O & O \\ \diagdown & | & \diagup \\ & R_{cell} & \end{bmatrix}_z$$

wherein:

$R_{cell}$ is the residue of an anhydroglucose repeat unit;

$z$ is from 50 to about 20,000; and each $R_1$, $R_2$ and $R_3$ is individually represented by the substituent structural formula:

$$+R_5O\}_m+R_6+O\}_y\}_n+R_7O\}_p+C_aH_{2a}\}_q R_8$$
$$\underset{R_{10}}{\overset{|}{R_9-N^+-R_{11}[A^-]\frac{1}{v}}}$$

wherein:

A is an anion;

a is an integer of from 1 to about 3;

m is an integer of from 0 to about 6;

n is an integer greater than or equal to 0, provided that the level of cationic substitution, CS, defined by the average moles of quaternary nitrogen atoms per mole anhydroglucose repeat unit is greater than 0;

p is an integer of from 0 to about 6;

q is 0 or 1;

each $R_5$ and $R_7$ is individually ethylene, a propylene or a hydroxypropylene;

$R_6$ is a di- or trivalent, cyclic, branched or straight chain, saturated or unsaturated hydrocarbon having from 2 to about 6 carbon atoms, provided there are at least 2 carbon atoms between the nitrogen atom and any oxygen atom;

$R_8$ is hydrogen, hydroxyl, $R_h$, alkyl, carboxyl or alkali metal or amine carboxylate, or other terminal group provided that when q is 0 then $R_8$ is hydrogen or alkyl;

each $R_9$, $R_{10}$ and $R_{11}$ is individually $R_h$, alkyl, aryl, aralkyl, alkaryl, cycloalkyl, alkoxyaryl or alkoxyalkyl, having at least two carbon atoms separating the oxygen atom in the alkoxyaryl or alkoxyalkyl group from the nitrogen atom or together with $R_6$ forms a heterocyclic ring;

$R_h$ is a hydrophobic group containing an alkyl group having at least 8 carbon atoms;

v is equal to the valence of A;

y is 0 or 1, provided that when y is 0 then p and q are 0 and $R_8$ is hydrogen or other terminal group.

6. The combination of claim 5 wherein the cellulose ether is polyquaternium-4, polyquaternium-10 or such cellulose ethers containing hydrophobic groups including polyquaternium-24.

7. The combination of claim 6 wherein the glycosaminoglycan is hyaluronan, hylan or other hyaluronan derivative.

8. A substantive combination of claim 1 wherein the glycosaminoglycan is substantive to keratinous material.

9. The combination of claim 8 having a relative weight ratio of cationic polymer to glycosaminoglycan which provides an enhanced degree of glycosaminoglycan substantivity.

10. The combination of claim 9 wherein the relative weight ratio of cationic polymer to glycosaminoglycan provides enhanced glycosaminoglycan substantivity to skin and is greater than about 5:1.

11. The combination of claim 9 wherein the relative weight ratio of cationic polymer to glycosaminoglycan provides enhanced glycosaminoglycan substantivity to hair and is from about 5:1 to about 25:1.

12. A compatible combination of claim 1 which provides an aqueous solution substantially free of precipitate.

13. A stable combination of claim 1 which provides an aqueous solution substantially free of precipitation or significant reduction in viscosity over a period of four months at 4° C.

14. A rheologically modified combination of claim 1 having a viscosity, elasticity or other rheological property of the glycosaminoglycan modified by the presence of the cationic polymer.

15. The combination of claim 14 wherein the glycosaminoglycan provides enhanced feel properties.

16. The combination of claim 1 wherein the relative weight ratio of cationic polymer to glycosaminoglycan is from about 0.01:1 to about 200:1.

17. The combination of claim 16 wherein the relative weight ratio of cationic polymer to glycosaminoglycan is from about 10:1 to about 50:1.

18. A hair or skin care composition or combination of compositions comprising the glycosaminoglycan and cationic polymer combination of claim 1 in one or more distinct formulations containing suitable hair or skin care ingredients.

19. A medical composition or combination of compositions comprising the glycosaminoglycan and cationic polymer combination of claim 1 in one or more distinct formulations containing suitable medical ingredients.

20. A combination comprising hyaluronan or derivative thereof and water-soluble, quaternary nigrogen-containing cellulose ether represented by the overall structural formula:

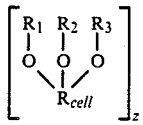

wherein:

R_{cell} is the residue of an anhydroglucose repeat unit;
z is from 50 to about 20,000; and
each $R_1$, $R_2$ and $R_3$ is individually represented by the substituent structural formula:

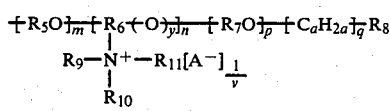

wherein:
A is an anion;
a is an integer of from 1 to about 3;
m is an integer of from 0 to about 6;
n is an integer greater than or equal to 0, provided that the level of cationic substitution, CS, defined by the average moles of quaternary nitrogen atoms per mole anhydroglucose repeat unit is greater than 0;
p is an integer of from 0 to about 6;
q is 0 or 1;
each $R_5$ and $R_7$ is individually ethylene, a propylene or a hydroxypropylene;
$R_6$ is a di- or trivalent, cyclic, branched or straight chain, saturated or unsaturated hydrocarbon having from 2 to about 6 carbon atoms, provided there are at least 2 carbon atoms between the nitrogen atom and any oxygen atom;
$R_8$ is hydrogen, hydroxyl, $R_h$, carboxyl or alkali metal or amine carboxylate, or other terminal group provided that when q is 0 then $R_8$ is hydrogen or other terminal group;
each $R_9$, $R_{10}$ and $R_{11}$ is individually $R_h$, alkyl, aryl, aralkyl, alkaryl, cycloalkyl, alkoxyaryl or alkoxyalkyl, having at least two carbon atoms separating the oxygen atom in the alkoxyaryl or alkoxyalkyl group from the nitrogen atom or together with $R_6$ forms a heterocyclic ring;
$R_h$ is a hydrophobic group containing an alkyl group having at least 8 carbon atoms;
v is equal to the valence of A;
y is 0 or 1, provided that when y is 0 then p and q are 0 and $R_8$ is hydrogen or other terminal group;
with the provisos that:
(1) the extent of hydrophobic group substitution, HS, defined by the average moles of said hydrophobic groups per mole of anhydroglucose repeat unit, is greater than 0; or
(2) any one of $R_9$, $R_{10}$ or $R_{11}$ taken together with $R_6$ forms a heterocyclic ring and the average value of n per anhydroglucose repeat unit, is greater than 0.

21. A process for modifying the properties of glycosaminoglycan which comprises combining glycosaminoglycan with an effective amount of cationic polymer.

22. The process of claim 21 which comprises increasing the substantivity of the glycosaminoglycan to keratinous material.

23. The process of claim 22 which comprises enhancing the feel characteristics provided by the glycosaminoglycan.

* * * * *

UNITED STATES PATENT AND TRADEMARK OFFICE
CERTIFICATE OF CORRECTION

PATENT NO. : 4,767,463
DATED : August 30, 1988
INVENTOR(S) : Brode et al.

It is certified that error appears in the above-identified patent and that said Letters Patent is hereby corrected as shown below:

In column 16 at line 40, "5-minutes" should read -- 5 1-minute --.

In Claim 1 at line 4, located in column 37 at line 2, "water-soluble of" should read -- of water-soluble --.

On the front page under "Assignee:" add -- and Biomatrix, Incorporated, Ridgefield, New Jersey. --.

Signed and Sealed this

Fourteenth Day of March, 1989

*Attest:*

*Attesting Officer*

DONALD J. QUIGG

*Commissioner of Patents and Trademarks*